(12) United States Patent
Keren et al.

(10) Patent No.: US 12,396,712 B2
(45) Date of Patent: Aug. 26, 2025

(54) SUTURING CLIP

(71) Applicant: Endomatic Ltd., Ariel (IL)

(72) Inventors: Dvir Keren, Tel Aviv (IL); Boaz Schwarz, Tel-Aviv (IL); Shimrit Markovitz, Tel Aviv (IL)

(73) Assignee: Endomatic Ltd., Or Yehuda (IL)

( * ) Notice: Subject to any disclaimer, the term of this patent is extended or adjusted under 35 U.S.C. 154(b) by 1012 days.

(21) Appl. No.: 17/050,444

(22) PCT Filed: Apr. 24, 2019

(86) PCT No.: PCT/IL2019/050461
§ 371 (c)(1),
(2) Date: Oct. 25, 2020

(87) PCT Pub. No.: WO2019/207585
PCT Pub. Date: Oct. 31, 2019

(65) Prior Publication Data
US 2021/0137507 A1    May 13, 2021

Related U.S. Application Data

(60) Provisional application No. 62/662,266, filed on Apr. 25, 2018.

(51) Int. Cl.
*A61B 17/00* (2006.01)
*A61B 17/064* (2006.01)
(Continued)

(52) U.S. Cl.
CPC .... *A61B 17/0057* (2013.01); *A61B 17/12122* (2013.01); *A61B 17/1227* (2013.01);
(Continued)

(58) Field of Classification Search
CPC ...................... A61B 17/0057; A61B 17/12122
See application file for complete search history.

(56) References Cited

U.S. PATENT DOCUMENTS

2003/0093096 A1* 5/2003 McGuckin, Jr. ... A61B 17/0057
606/151
2003/0220667 A1   11/2003 van der Burg et al.
(Continued)

FOREIGN PATENT DOCUMENTS

| CN | 104000627 | 8/2017 |
| EP | 1512383 | 3/2005 |

(Continued)

OTHER PUBLICATIONS

International Search Report and the Written Opinion Dated Mar. 16, 2023 From the International Searching Authority Re. Application No. PCT/IL2022/051299 (16 Pages).
(Continued)

*Primary Examiner* — Erin Mcgrath

(57) ABSTRACT

Suturing clips which may be guided to a heart by a transvascular/trans-septal approach, and yet operate to close the left atrial appendage (LAA) from a position located entirely within the LAA are described. Arms of suturing clips constructed of a superelastic alloy are expanded from a catheter delivery system, anchored within the LAA and/or ostium of the LAA, and then collapsed again to a suturing configuration. Collapse is optionally by a reverting mechanism, wherein arms are constrained to collapse back in a direction reverse to their original expansion; or by an everting mechanism, wherein arm portions move past their expanded position to close with each other on an opposite side of their original position. In some embodiments, delivery systems include further elements to assist in clip placement at the LAA, for example a spreader for spreading the LAA, and/or a stopper for preventing deep intrusion to the LAA.

21 Claims, 22 Drawing Sheets

(51) Int. Cl.
  *A61B 17/12* (2006.01)
  *A61B 17/122* (2006.01)
  *A61B 17/128* (2006.01)

(52) U.S. Cl.
  CPC .............. *A61B 17/1285* (2013.01); *A61B 2017/00584* (2013.01); *A61B 2017/00592* (2013.01); *A61B 2017/00623* (2013.01); *A61B 2017/00632* (2013.01); *A61B 2017/0641* (2013.01)

(56) References Cited

U.S. PATENT DOCUMENTS

| | | | |
|---|---|---|---|
| 2004/0087985 A1 | 5/2004 | Loshakove et al. | |
| 2007/0156123 A1* | 7/2007 | Moll | A61B 17/068 606/1 |
| 2007/0198057 A1* | 8/2007 | Gelbart | A61B 17/0057 606/213 |
| 2013/0090672 A1* | 4/2013 | Butler | A61B 5/0215 606/151 |
| 2013/0225900 A1* | 8/2013 | Kalloo | A61B 17/0057 606/154 |
| 2014/0018831 A1 | 1/2014 | Kassab et al. | |
| 2017/0340329 A1 | 11/2017 | Groothuis et al. | |
| 2018/0242960 A1 | 8/2018 | Kalloo et al. | |

FOREIGN PATENT DOCUMENTS

| | | |
|---|---|---|
| EP | 2656816 | 10/2013 |
| EP | 3597150 | 1/2020 |
| JP | 2003-509175 | 3/2003 |
| JP | 2003-512128 | 4/2003 |
| JP | 2009-504326 | 2/2009 |
| WO | WO 01/21247 | 3/2001 |
| WO | WO 03/101310 | 12/2003 |
| WO | WO 2012/126477 | 9/2012 |
| WO | WO 2019/207585 | 10/2019 |
| WO | WO 2023/105523 | 6/2023 |

OTHER PUBLICATIONS

International Preliminary Report on Patentability Dated Nov. 5, 2020 From the International Bureau of WIPO Re. Application No. PCT/IL2019/050461. (16 Pages).
International Search Report and the Written Opinion Dated Oct. 16, 2019 From the International Searching Authority Re. Application No. PCT/IL2019/050461. (23 Pages).
Invitation to Pay Additional Fees, Communications Relating to the Results of the Partial International Search and the Provisional Opinion Dated Aug. 19, 2019 From the International Searching Authority Re. Application No. PCT/IL2019/050461. (16 Pages).
Notice of Reason(s) for Rejection Dated Apr. 4, 2023 From the Japan Patent Office Re. Application No. 2020-560318 and Its Translation Into English. (6 pages).
Notification of Office Action and Search Report Dated Jan. 26, 2024 From the National Intellectual Property Administration of the People's Republic of China Re. Application No. 201980034857.6 and Its Machine Translation Into English. (16 Pages).
Summary Dated Feb. 5, 2024 of Notification of Office Action and Search Report Dated Jan. 26, 2024 From the National Intellectual Property Administration of the People's Republic of China Re. Application No. 201980034857.6. (6 Pages).
Notification of Office Action and Search Report Dated May 30, 2024 From the National Intellectual Property Administration of the People's Republic of China Re. Application No. 201980034857.6 and Its Translation Into English. (15 Pages).
Communication Pursuant to Article 94(3) EPC Dated May 27, 2024 From the European Patent Office Re. Application No. 19724257.1 (10 Pages).
English Summary Dated Jun. 6, 2024 of Notification of Office Action and Search Report Dated May 30, 2024 From the National Intellectual Property Administration of the People's Republic of China Re. Application No. 201980034857.6. (4 Pages).
International Preliminary Report on Patentability Dated Jun. 20, 2024 From the International Bureau of WIPO Re. Application No. PCT/IL2022/051299 (11 Pages).
Examination Report Dated Apr. 17, 2024 From the Australian Government, IP Australia Re. Application No. 2019259934. (3 Pages).
Office Action Dated Sep. 20, 2023 From the Israel Patent Office Re. Application No. 278284. (5 Pages).
Office Action Dated Aug. 28, 2024 From the Israel Patent Office Re. Application No. 278284. (7 Pages).

\* cited by examiner

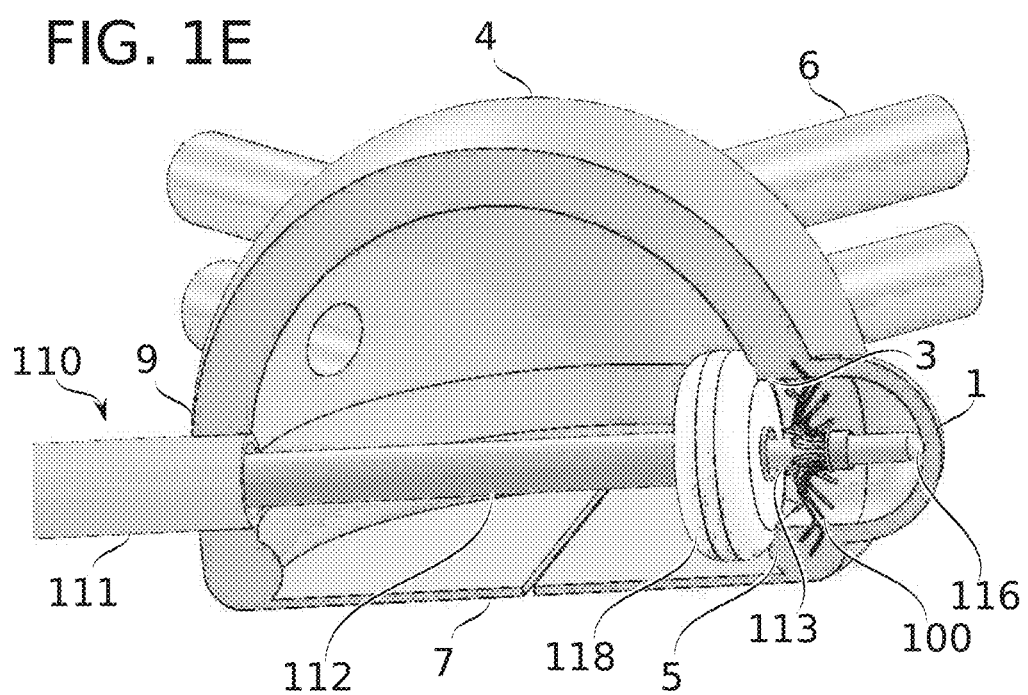

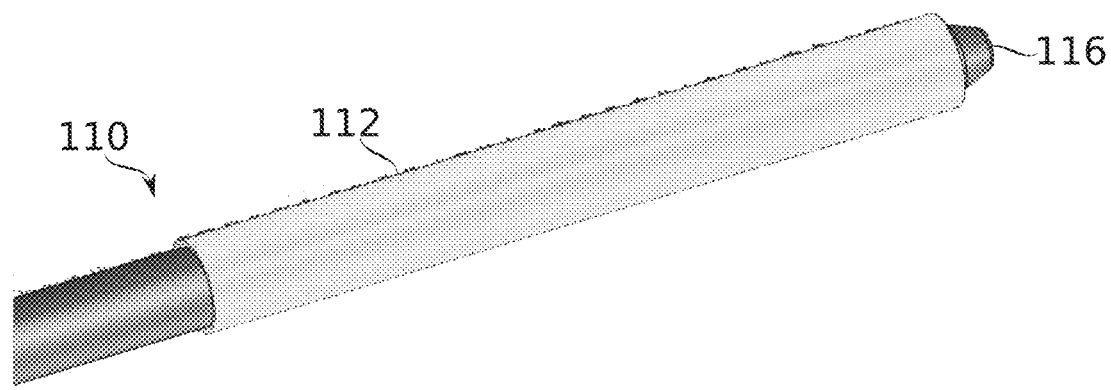
FIG. 2M
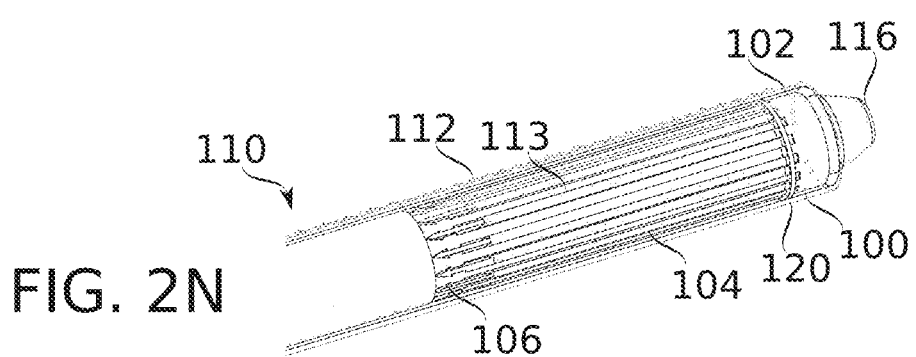
FIG. 2N
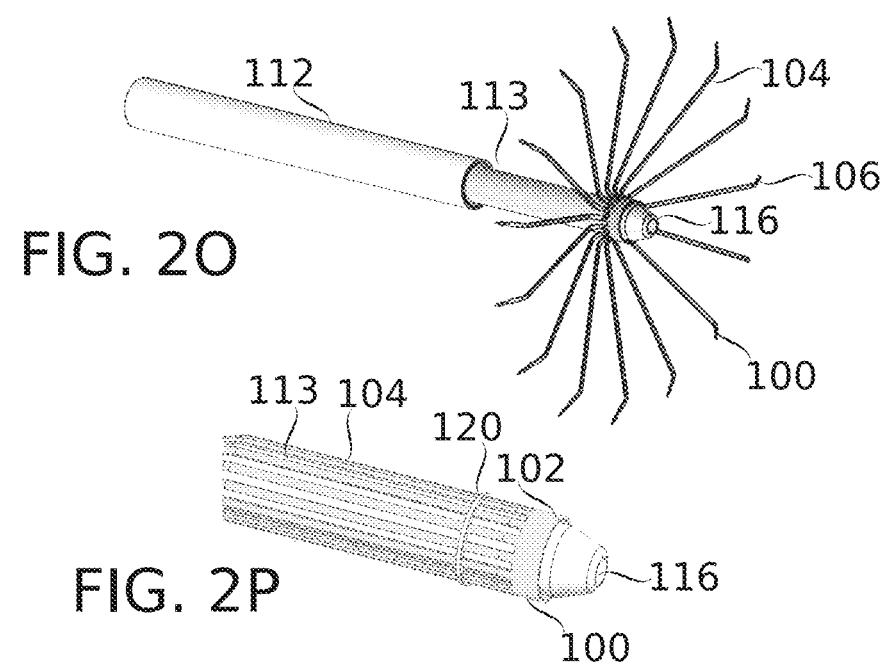
FIG. 2O
FIG. 2P

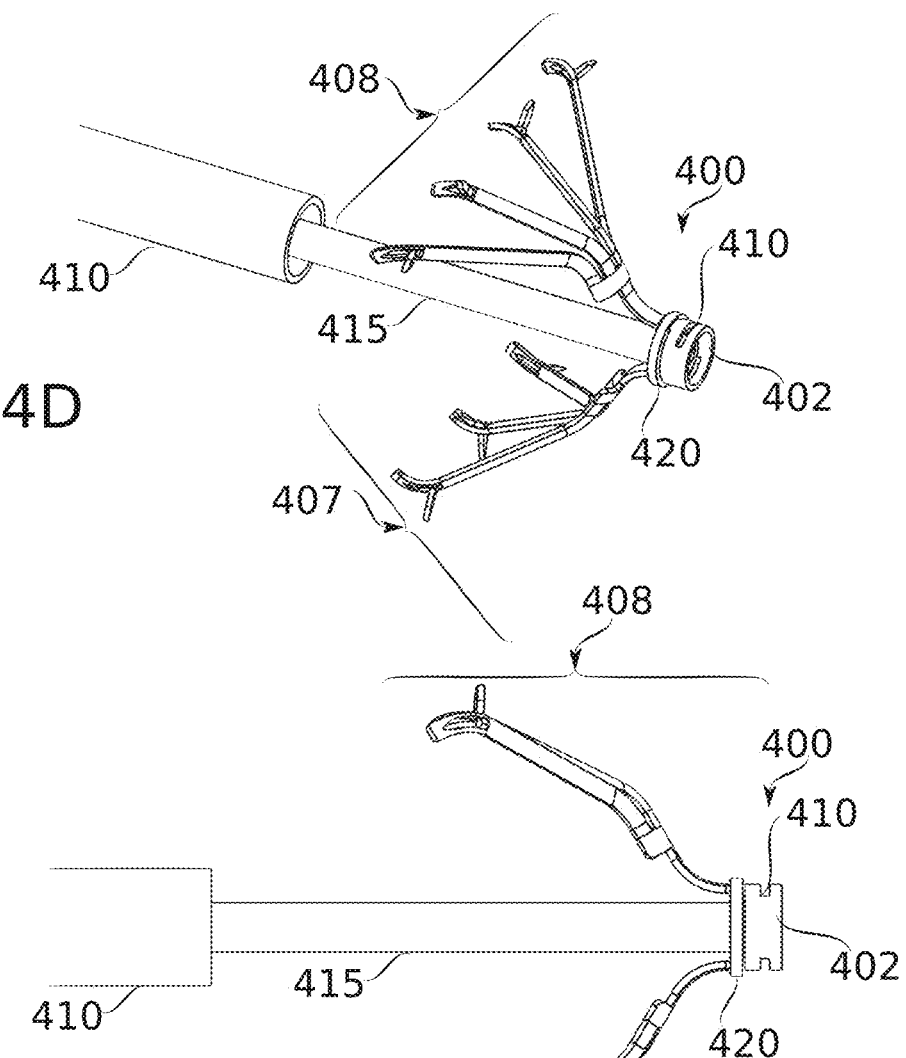
FIG. 4D
FIG. 4E
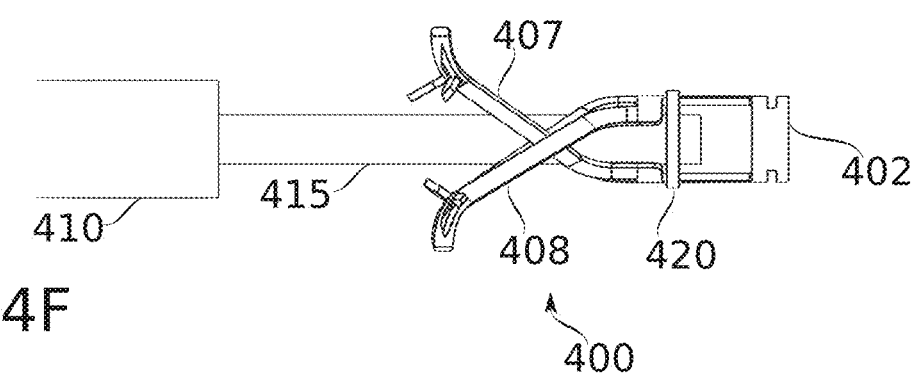
FIG. 4F

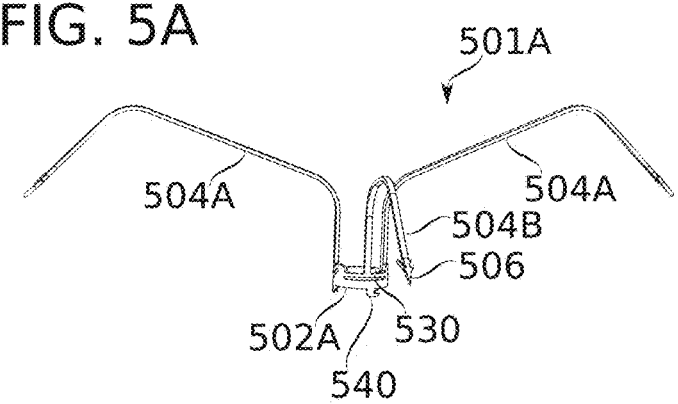
FIG. 5A
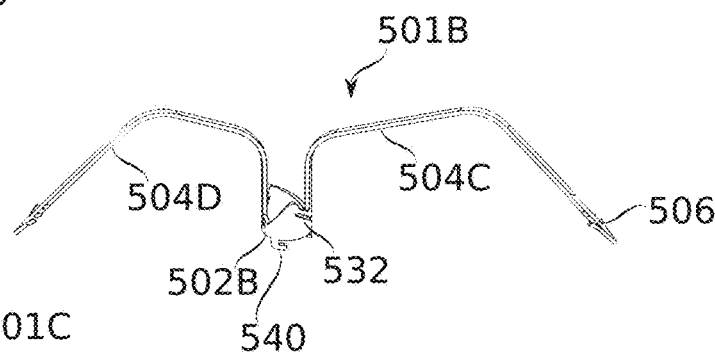
FIG. 5B
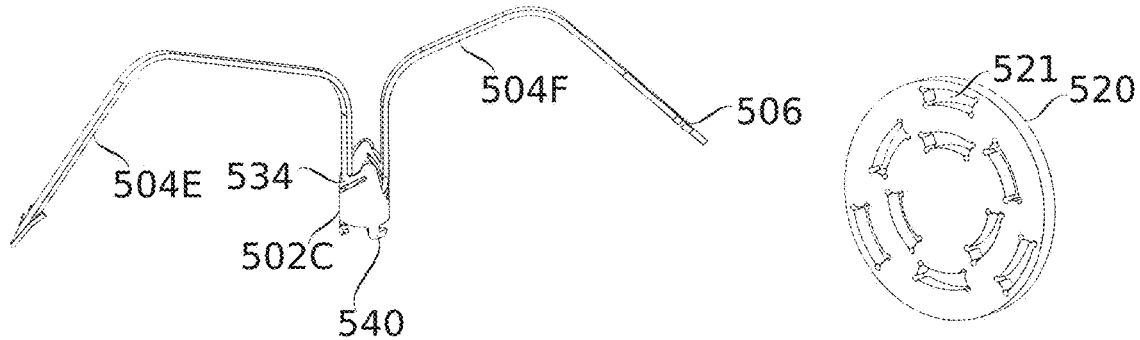
FIG. 5C
FIG. 5D
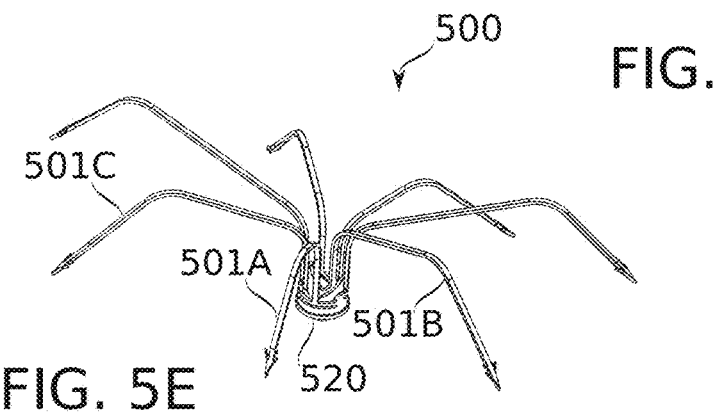
FIG. 5E

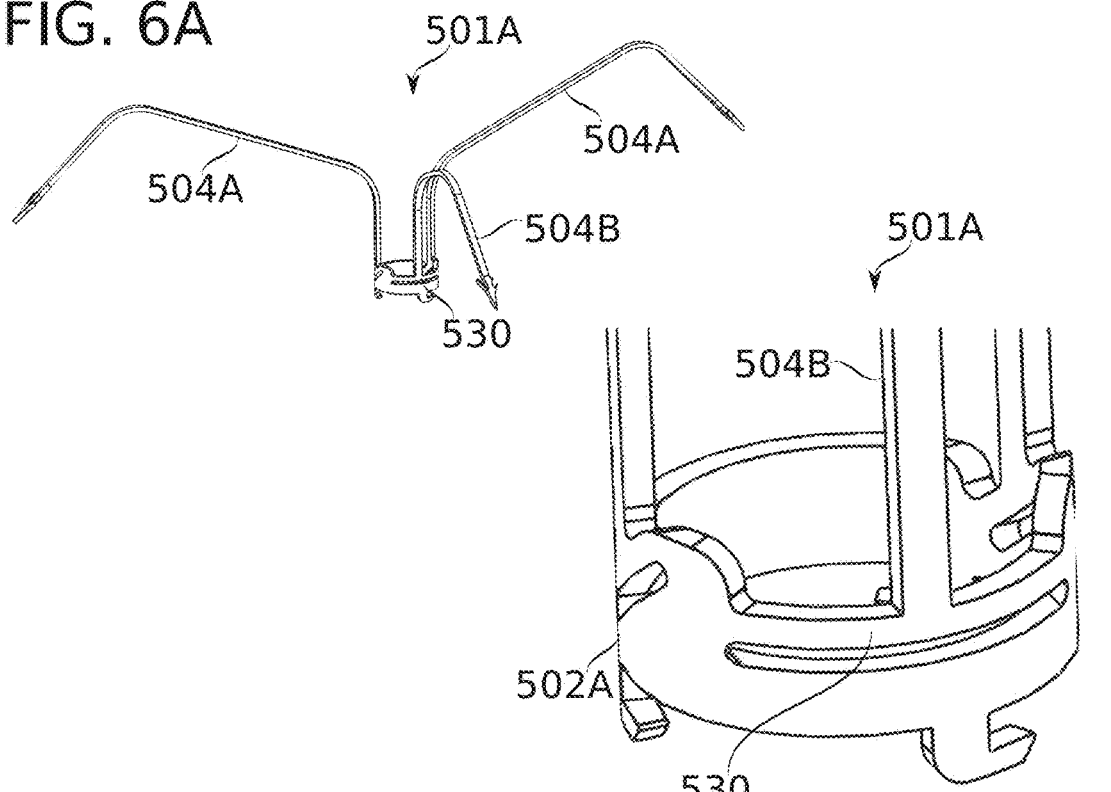
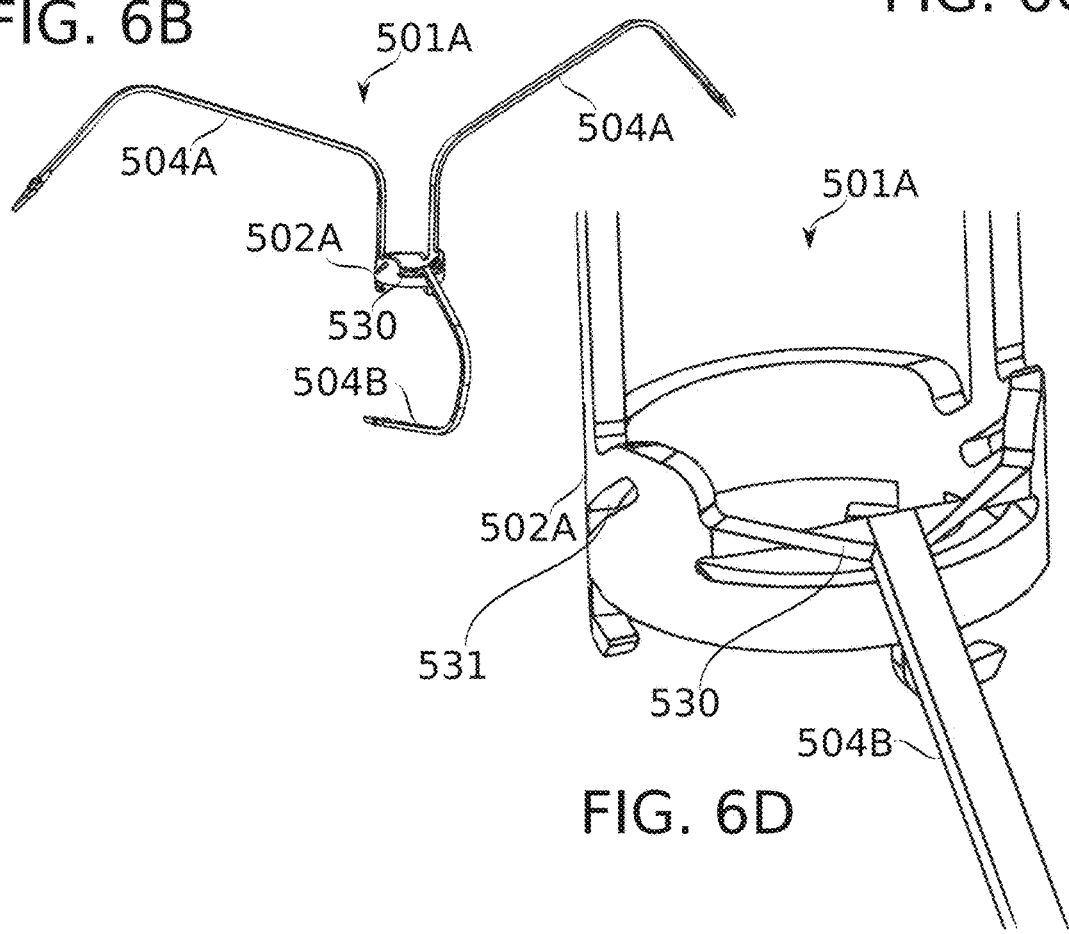

SUTURING CLIP

RELATED APPLICATIONS

This application is a National Phase of PCT Patent Application No. PCT/IL2019/050461 having International filing date of Apr. 24, 2019, which claims the benefit of priority under 35 USC § 119 (e) of U.S. Provisional Patent Application No. 62/662,266 filed on April 25, 2018. The contents of the above applications are all incorporated by reference as if fully set forth herein in their entirety.

FIELD AND BACKGROUND OF THE INVENTION

The present invention, in some embodiments thereof, relates to the field of closure devices for medical use, and more particularly, to closure devices for use in the LAA.

The medical community considers the left atrium appendage (LAA) as a potential causal locus for CVA (cardiovascular accident) due to the potential of the LAA for embolic creation.

Closing off the LAA may be performed, for example in an open thoracic approach or by a minimally invasive trans-vascular (and typically trans-septal) approach. In the open approach, a surgeon is likely to suture the ostium (the connection between the LAA and the left atrium). In a trans-vascular approach, an interventional cardiologist doesn't open the patient's chest, and seals the LAA, e.g., using a plug and/or stent-like construction deployed inside the LAA. The principle is that reduction of atrial wall irregularities and/or circulatory dead zones may reduce a potential for thrombogenesis.

SUMMARY OF THE INVENTION

There is provided, in accordance with some embodiments of the present disclosure, a suturing clip for closing a body lumen aperture, comprising: a plurality of arms each joined at a basal side of the arm to a core of the suturing clip; and a respective anchor at a terminal end of each arm; wherein the suturing clip is configured to convert between: a collapsed delivery configuration; an expanded anchoring configuration having a diameter at least 5× larger than a diameter of the suturing clip in the collapsed delivery configuration, and a collapsed suturing configuration shaped to re-position the anchors where they close tissue of an aperture perimeter after the tissue is attached by contact with the anchors in the expanded anchoring configuration; wherein the suturing clip, in the collapsed delivery configuration, is configured to attach to a delivery mount and be advanced on the delivery mount into the body lumen aperture by distal movement along a proximal-to-distal axis of the suturing clip; and wherein the anchors of the suturing clip, in the collapsed suturing configuration, are positioned proximal to the core along the proximal-to-distal axis.

In some embodiments, the suturing clip resiliently self-expands from the collapsed delivery configuration to the expanded anchoring configuration.

In some embodiments, the delivery mount is configured to be detached from the suturing clip in the collapsed suturing configuration and withdrawn through tissue closed by the anchors of the suturing clip to the side of the closed tissue opposite the suturing clip.

In some embodiments, the suturing clip is configured to resiliently self-collapse from the expanded anchoring configuration to the collapsed suturing configuration.

In some embodiments, the suturing clip is configured to resiliently self-collapse from the expanded anchoring configuration to the collapsed suturing configuration.

In some embodiments, the suturing clip in the collapsed delivery configuration is sheathed within the sheathing lumen.

In some embodiments, the suturing clip is configured to resiliently self-expand from the collapsed delivery configuration to the expanded anchoring configuration upon a partial unsheathing from the sheathing lumen.

In some embodiments, the suturing clip is configured to resiliently self-collapse from the expanded anchoring configuration to the collapsed suturing configuration upon a further unsheathing from the sheathing lumen.

In some embodiments, the suturing clip is configured to evert during converting between the collapsed delivery configuration and the expanded anchoring configuration, so that a side of the anchors which face radially inward in the collapsed delivery configuration faces outward in the expanded anchoring configuration.

In some embodiments, the suturing clip is configured to evert during converting between the collapsed delivery configuration and the collapsed suturing configuration, so that a portion of the arms which is initially on a distal side of the core moves to a proximal side of the core.

In some embodiments, the suturing clip collapses from the expanded anchoring configuration to the collapsed suturing configuration upon a movement of the closure disk.

In some embodiments, the closure disk moves from a position nearer to the core of the suturing clip to a position further from the core to collapse the suturing clip from the expanded anchoring configuration to the collapsed suturing configuration upon a movement of the closure disk.

In some embodiments, conversion from the expanded anchoring configuration to the collapsed suturing configuration comprises a reverting movement of the arms in a direction opposite a direction of their expansion from the collapsed delivery configuration to the expanded anchoring configuration.

In some embodiments, the suturing clip is provided together with a spreader, separately actuatable to extend laterally from the trans-vascular catheter, insert to the body lumen aperture, and is configured to contact tissue of the body lumen aperture with grips to set a position of the sheathing lumen from which the suturing clip is deployed.

In some embodiments, the suturing clip is unsheathed by a proximal movement of the sheath relative to the suturing clip, and the suturing clip is oriented in the sheath along a proximal-distal axis, with the core on a proximal side of the suturing clip, and the anchors on a distal side of the suturing clip.

In some embodiments, the suturing clip is unsheathed by a proximal movement of the sheath relative to the suturing clip, and the suturing clip is oriented in the sheath along a proximal-distal axis, with the anchors on a proximal side of the suturing clip, and the core on a distal side of the suturing clip.

In some embodiments, the anchors, in the collapsed suturing configuration, define a zigzag pattern extending along a band of closure of the closed tissue.

In some embodiments, the anchors, in the collapsed suturing configuration, draw tissue to a surgical purse-string configuration.

In some embodiments, the arms extend from the core, each from an individual base attached to the core.

In some embodiments, a first plurality of the arms extends from the core via a trunk which is shared in common by the plurality of the arms.

In some embodiments, arms of the first plurality are configured to interdigitate with arms of the second plurality in the collapsed suturing configuration.

In some embodiments, a material of the arms comprises a nitinol alloy.

In some embodiments, a material of the suturing clip comprises a radiopaque marker more radiopaque than nitinol.

In some embodiments, at least one of the arms is mounted to at least one side of the torsion bar, and the torsion bar is configured to twist to move the at least one of the arms from the collapsed delivery configuration toward the collapsed final configuration.

In some embodiments, at least one of the arms is configured to bend along a longitudinal extent of the arm to move the at least one of the arms from the collapsed delivery configuration toward the collapsed final configuration.

There is provided, in accordance with some embodiments of the present disclosure, a suturing clip for closing a body lumen aperture, comprising: a plurality of arms each joined at a basal side of the arm to a core of the suturing clip; a respective anchor at a terminal end of each arm; and a closure disk; wherein the suturing clip is configured to convert between: a collapsed delivery configuration sized to be sheathed by a sheathing lumen of a trans-vascular catheter; an expanded anchoring configuration having a diameter at least 5× larger than a sheathed diameter of the suturing clip in the collapsed delivery configuration, and a collapsed suturing configuration shaped to re-position the anchors where they close tissue of an aperture perimeter after the tissue is attached by contact with the anchors in the expanded anchoring configuration; and wherein the closure disk is movable along a distal-proximal axis of the suturing clip to actuate conversion between expanded anchoring configuration and the collapsed suturing configuration.

There is provided, in accordance with some embodiments of the present disclosure, a suturing clip for closing a body lumen aperture, comprising: a plurality of arms each joined at a basal side of the arm to a core of the suturing clip; and a respective anchor at a terminal end of each arm; and wherein the suturing clip is configured to convert between: an expanded anchoring configuration positioning at least two anchors on one side of a perimeter, and at least one anchor on another side of the perimeter, and a collapsed suturing configuration repositioning the anchors from the expanded anchoring configuration by movement of the at least one anchor to cross between the at least two anchors.

In some embodiments, the at least two anchors comprises at least four anchors, and the at least one anchors comprises at least three anchors; and the collapsed suturing configuration repositions the anchors from the expanded anchoring configuration by moving each of the at least three anchors to cross between respective pairs of the at least four anchors.

There is provided, in accordance with some embodiments of the present disclosure, a suturing clip for closing a body lumen aperture, comprising: a plurality of arms each joined at a basal side of the arm to a core of the suturing clip; and a respective anchor at a terminal end of each arm; wherein the suturing clip is configured to convert between: a collapsed delivery configuration expandable to attach the anchors to tissue of the body lumen aperture, and a collapsed suturing configuration shaped to re-position the anchors where they close the body lumen aperture by movement of the attached tissue; and wherein the anchors are distal to the core in the collapsed delivery configuration, and proximal to the core in the collapsed suturing configuration, while the core remains in a same proximal-to-distal orientation in the two configurations.

In some embodiments, the arms are configured to evert while re-positioning the anchors between the collapsed delivery configuration and the collapsed suturing configuration.

In some embodiments, the anchors are positioned on a radially inward side of the arms in the collapsed delivery configuration, and move to a radially outward side of the arms during movement of the arms toward the collapsed suturing configuration.

There is provided, in accordance with some embodiments of the present disclosure, a device for deploying within a body lumen aperture, comprising: a plurality of arms each joined at a basal side of the arm to a core of the device; and a respective terminal end of each arm; wherein the device is configured to convert between: a collapsed delivery configuration with the terminal ends in a first configuration; a collapsed final configuration shaped to re-position the terminal ends to a second configuration; and a torsion bar; wherein at least one of the arms is mounted to at least one side of the torsion bar, and the torsion bar is configured to twist to move the at least one of the arms from the collapsed delivery configuration toward the collapsed final configuration.

In some embodiments, the device is a suturing clip comprising a respective anchor at each terminal end; and wherein: the collapsed delivery configuration is expandable to attach the anchors to tissue of the body lumen aperture; and the collapsed suturing configuration re-positions the anchors where they close the body lumen aperture by movement of the attached tissue.

In some embodiments, the torsion bar is located where the at least one of the arms are joined at the basal side of the arm to the core.

In some embodiments, the torsion bar is located between two segments of the at least one of the arms.

There is provided, in accordance with some embodiments of the present disclosure, a method of closing a body lumen aperture, comprising: advancing a suturing clip attached to a delivery mount through the body lumen aperture from a first side of the body lumen aperture to a second side of the body lumen aperture; expanding the suturing clip at least partially on the second side of the body lumen aperture; anchoring tissue defining a perimeter of the body lumen aperture to anchors of the suturing clip; and collapsing the suturing clip so that the anchors close the body lumen aperture while the suturing clip remains on the second side of the closed body lumen aperture.

In some embodiments, the suturing clip remains entirely on the second side of the closed body lumen aperture.

In some embodiments, the suturing clip is unexposed to contents of the body lumen on the first side of the closed body lumen aperture after the collapsing.

In some embodiments, the method comprises withdrawing the delivery mount through the closed body lumen aperture to the first side of the body lumen aperture, while the suturing clip remains on the second side of the body lumen aperture, and the body lumen aperture remains closed by the collapsed suturing clip.

In some embodiments, the body lumen aperture is an ostium of a left atrial appendage.

In some embodiments, the advancing comprises advancing the delivery mount through a trans-vascular route to reach the first side of the body lumen aperture.

In some embodiments, the advancing comprises advancing the delivery mount through a heart septal wall to reach the first side of the body lumen aperture.

In some embodiments, the first side is an atrial side of an ostium of an LAA, and the second side is within the LAA.

In some embodiments, the collapsing closes the only aperture leading to the second side of the body lumen aperture.

In some embodiments, the expanding comprises unsheathing at least a portion of the arms of the suturing clip and allowing the arms to resiliently self-expand.

In some embodiments, the collapsing comprises unsheathing a portion of the arms of the suturing clip and allowing the arms to resiliently self-collapse.

In some embodiments, the collapsing comprises operating a closure disk to force the arms to a less-expanded diameter.

In some embodiments, the collapsing comprises moving the anchors into a zigzag configuration.

In some embodiments, the collapsing comprises moving the anchors toward a common radial center.

In some embodiments, the collapsing comprises moving at least one of the anchors radially outward, while at least one of the anchors moves radially inward.

Unless otherwise defined, all technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the present disclosure are herein described, by way of example only, with reference to the accompanying drawings. With specific reference now to the drawings in detail, it is stressed that the particulars shown are by way of example, and for purposes of illustrative discussion of embodiments of the present disclosure. In this regard, the description taken with the drawings makes apparent to those skilled in the art how embodiments of the present disclosure may be practiced.

In the drawings:

FIG. 1E schematically illustrates a trans-septal approach insertion of a suturing clip using a delivery system, according to some embodiments of the present disclosure;

FIGS. 2M-2P illustrate details of interactions between a delivery system and a suturing clip, according to some embodiments of the present disclosure;

FIGS. 4D-4H show deployment of a suturing clip under control of a deployment system, including deployment member, according to some embodiments of the present disclosure;

FIGS. 5A-5D schematically illustrate parts of an everting suturing clip, according to some embodiments of the present disclosure;

FIGS. 5E-5F schematically illustrate an assembled suturing clip in an expanded configuration, according to some embodiments of the present disclosure;

FIGS. 6A-6D schematically illustrate torsion bar arm mountings, according to some embodiments of the present disclosure;

DESCRIPTION OF SPECIFIC EMBODIMENTS OF THE INVENTION

Figures 1A, 1B:
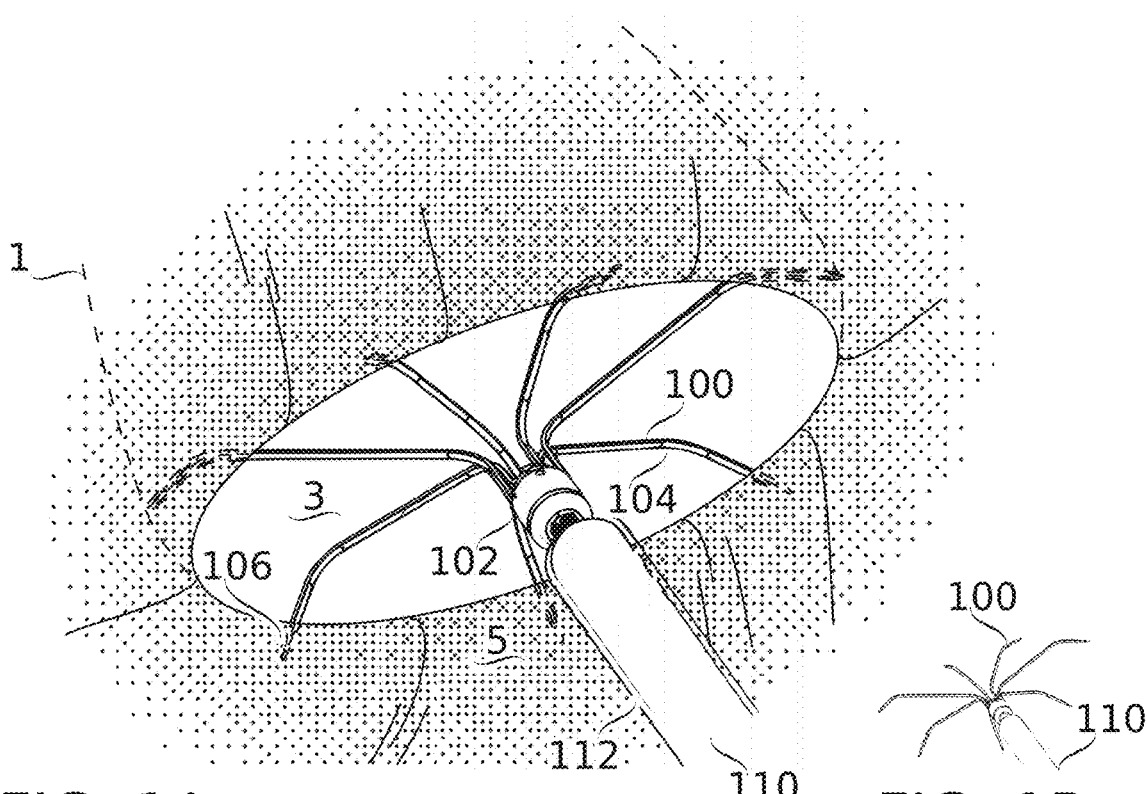
FIG. 1A schematically illustrates a suturing clip engaged to tissue within a LAA, according to some embodiments of the present disclosure.
FIG. 1B schematically illustrates the suturing clip of FIG. 1A in an expanded configuration suitable for tissue engagement, according to some embodiments of the present disclosure.

The present invention, in some embodiments thereof, relates to the field of closure devices for medical use, and more particularly, to closure devices for use in the LAA.

Overview

An aspect of some embodiments of the present disclosure relates to suturing clips configured for closure of an aperture from an opposite side of the aperture than the side from which the suturing clip is introduced to the aperture, and methods of use thereof.

In some embodiments, a suturing clip is configured to close a left atrial appendage (LAA) in a heart. Closure of the LAA is performed in some patients for mitigation of the thrombogenic potential of the LAA. The suturing clips, in some embodiments, operate to close the LAA from a position ultimately situated entirely within the LAA. This provides a potential advantage by mimicking an advantage of the suturing technique of LAA closure; insofar as it closes the ostium without (or with minimal) artificial material left exposed inside the atrium wall. Artificial material is potentially thrombogenic, increasing a risk for a CVA and/or creating an indication for supporting treatment by Coumadin or another anticoagulant.

The clip also provides the potential advantages of placement via a trans-vascular (minimally invasive) approach. Using a catheter, the suturing clip is introduced (e.g., via a trans-septal approach) into the LAA. It is then expanded inside the LAA and attached to the LAA opening (ostium). Then the clip is collapsed to a suturing configuration which closes the LAA. Upon collapse to the suturing configuration, the suturing clip remains inside the LAA, isolated from the general circulation. The LAA is transformed thereby into a closed lumen, with no open passageway leading into or out of a pocket defined by tissue of the LAA<and in which the suturing clip is contained.

In some embodiments, flexible components of suturing clips (including flexible arms and/or hinges of such suturing clips) are constructed from a superelastic alloy such as nitinol. Superelasticity is associated with resilient deformation up to an unusually high maximum strain (e.g., 7%-13%); considering that superelastic materials nonetheless have a high elastic modulus (resistance to elastic deformation) typical of a structural metal such as titanium or steel; for example, an elastic modulus in the range of 20-100 GPA. This provides superelastic materials with the potential to store considerable energy by their deformation (e.g., energy convertible to closing force), particularly compared to constructions of similar dimensions made from other materials.

Without commitment to a particular mechanism or theory, superelasticity in metal alloys is understood to comprise an elastically resilient response to applied stress, related to reversible movements during phase transformation of a crystal; e.g., between the austenitic and martensitic phases of the crystal.

Herein, the "superelastically set" shape, configuration, and/or position of a component refers to the shape the unconstrained component tends to assume. The shape may be set (sometimes also referred to as "memorized") during manufacture, for example, by bracing the component in its targeted shape, and heating it above the critical temperature for resetting its superelastic shape.

Superelasticity is also referred to as "pseudoelasticity". Superelastic alloys may additionally have a shape-memory property, whereby the superelasticity is evidenced within a certain range of conditions (e.g., a temperature range). Outside that range, the alloy is more deformable; but when brought back into the superelastic range, the alloy returns to its superelastically set shape.

The common name "nitinol" refers to a range of superelastic nickel-titanium alloys (instances of which have different ratios of nickel and titanium) with well-accepted properties of biocompatibility. Some superelastic materials may include additional elements, and/or be based on a different system of alloyed elements. For example superelastic alloys based on the systems Fe—Ni—Al, Cu—Zn—Al, Fe—Mn—Si, and Cu—Al—Ni (optionally in combination with further elements) have been described. Superelastic materials incorporating polymers (e.g., polymer-coated nitinol) have also been described. Insofar as other examples and/or types of superelastic materials may become available, embodiments of the current disclosure are optionally adapted to use them.

Accordingly, the high-strain resilience of superelastic components allows large conformational changes. Their high elastic modules causes those conformational changes to proceed while exerting resilient force that can be significant enough to drag attached tissue along with, and/or otherwise applied, for example to assist in gaining an anchoring purchase on tissue. Suturing clips, during deployment to a target aperture such as the ostium of an LAA, pass between:

A collapsed delivery configuration, small enough for trans-vascular delivery, for example, small enough to fit in a delivery tube having a lumen diameter 5 mm in diameter or less, 4 mm in diameter or less, 3 mm in diameter or less, and/or to fit within another diameter, optionally in a range of about 3-5 mm.

An expanded anchoring configuration, which positions tissue anchoring elements (anchors) where they can be attached to tissue. In some embodiments, the expanded anchoring configuration expands to a maximum of at least 15 mm, 20 mm, 25 mm, 30 mm, or another diameter. In some embodiments, the expanded anchoring configuration is at least 4×, 5×, 6×, 7×, 8×, 9×, 10×, or another factor larger than a diameter of the suturing clip in the collapsed delivery configuration.

A collapsed suturing configuration, which brings the tissue anchoring elements toward one another to create a closure, for example as a band-type, or a surgical purse-string-type closure.

In some embodiments, elements undergoing conformation changes comprise arms, attached via a common base or "core" of the suturing clip. An attached side of an arm is also referred to herein as a "basal side" of the arm. The arms may themselves be flexible, and/or they may be attached to the core via a flexible element such as a torsion spring. The suturing clip comprises, for example, 2-20 arms; for example, 2, 5, 7, 10, 13, 15 or another number of arms.

In some embodiments, one or more of the transformations is configured so that it is self-actuated by resilient forces acting from within the superelastic material of the suturing clip. For example, the suturing clip is resiliently self-expanding from the collapsed delivery configuration to the expanded anchoring configuration, and/or resiliently self-collapsing from the expanded anchoring configuration to the collapsed suturing configuration. The resilient forces tend to restore positions of the arms (and in particular, the anchors they carry) to a superelastically set shape of the suturing clip, optionally in one or more stages of expansion and/or collapse.

In some embodiments, one or more of the transformations is initiated by the addition, removal, and/or movement of a constraining device. For example, resilient self-expanding and/or self-collapse of the suturing clip is optionally initiated by at least partial unsheathing of the suturing clip from a sheath (acting as the constraining device). In some embodiments, expansion and/or collapse is induced by movement of a controlling component, for example a closure disk which is attached to the arms in a way that restricts their expansion diameter, e.g., by passage of each arm through an aperture of the closure disk. As the closure disk moves proximally or distally (for example), the arms are constrained to close or open.

In some embodiments, the transformations are actuated by operation of a relatively long and narrow control member, which passes through the aperture targeted for closure and attaches to the suturing clip. The suturing clip, once collapsed to its collapsed suturing configuration, remains on a distal side of the closure, opposite the side from which it was originally introduced. The control member is withdrawn to that opposite side when closure is complete. The small gap forced by the control member's earlier presence is closed over when it withdraws, due to closure forces exerted by the collapsed suturing clip.

While examples of the use of the suturing clips are presented herein with special reference to closure of the LAA, it should be understood that clips are optionally used, changed as necessary, for closure of other body lumens; for example, appendix, fistulas, and/or gastric restriction. Embodiments of suturing clips may also be used, for example, in reverse-side suturing of wounds and/or surgical incisions and/or punctures. For example, a GI lumen may be closed by a suturing clip deployed via intraperitoneal (e.g., laparoscopic) access, optionally with later removal of the suturing clip via an endoluminal (e.g., endoscopic) access. Conversely, deployment of a suturing clip is optionally performed via an endoluminal access to an outside of the lumen, and retrieval (if performed) is from an access outside the lumen. This may be useful, for example, as a planned and/or emergency method of using access from the "wrong side" of an opening to nevertheless achieve closure of that opening. In another example, skin may be reverse-side sutured with potential advantages for security of attachment and/or later aesthetic appearance, optionally with later retrieval of the reverse-side suturing clip via laparoscopic access from another access port. Closure may be performed jointly from two sides of an aperture, and optionally one direction of access. In some embodiments, suturing clips are configured for creating closures in non-surgical situations, for example to effect hidden repairs on fabrics and/or membranous articles, and/or position and clamp such articles for receiving such repairs.

In some embodiments, arms of a suturing clip comprise anchors, configured to engage with tissue, so that force exerted on the anchors moves the tissue into new positions. Optionally, the anchors are shaped as barbs, hooks, spikes, or other shapes. In some embodiments, anchors operate by hinging or flexing differently depending on direction of motion (in the style, for example, of a toggling harpoon). For example, an anchor may be hinged or otherwise constructed so that upon receiving force in a direction for insertion, it holds stiff, but upon receiving a tugging force in the opposite direction, the hinge or flex activates, so that a portion of the anchor turns or expands and can no longer be easily dragged out of the hole through which it entered. Additionally or alternatively, an anchor may be hinged and/or flex so that it becomes radially smaller as it advances into a self-created aperture upon insertion, but otherwise expands and/or tends to be forced into a radially expanded state upon the exertion of force in a reverse direction.

A potential advantage of an actuated suturing clip, compared, e.g., to suturing by needle and thread, is decreased complexity for deployment. With relatively few fine control actions necessary, the surgeon's task is potentially made easier, more reliable, and/or performable with a reduced requirement for training and/or experience.

An aspect of some embodiments of the present disclosure relates to suturing clips configured for reverting closure of an aperture from an opposite side of the aperture than the side from which the suturing clip is introduced to the aperture. In some embodiments, reverting closure closes the only aperture leading to the side of the body lumen aperture in which the suturing clip remains, sealing it within a closed chamber.

In some embodiments, arms of a suturing clip inserted to a body lumen are expanded from a first, collapsed configuration to reach a second, expanded configuration. In the expanded configuration, the suturing clip is manipulated to recruit tissue of the body lumen by attachment thereto. Optionally, recruitment is by attachment of anchors positioned by the expanded arms to a predefined pattern, e.g., to a pattern complementary to a shape of the tissue being anchored in, and/or to a pattern which can be manipulated by relatively simple and/or stereotyped movements in order to achieve reliable attachment.

From the expanded configuration, the device is actuated to achieve closure. Closure, in some embodiments, comprises movement of the attachment points to a new configuration, by a motion which reverses (reverts) a direction of arm and/or anchor movement during expansion to the expanded configuration.

In some embodiments, the movement of the attachment points is actuated by manipulation of a constraining device, such as a disk, ring, or other form of clamp, which constrains a maximum radius of radial expansion as it moves along a length of the device.

An aspect of some embodiments of the present disclosure relates to suturing clips configured for everting closure of an aperture from an opposite side of the aperture than the side from which the suturing clip is introduced to the aperture. In some embodiments, everting closure closes the only aperture leading to the side of the body lumen aperture in which the suturing clip remains, sealing it within a closed chamber.

In some embodiments, arms of a suturing clip inserted to a body lumen are expanded from a first, collapsed configuration to reach a second, expanded configuration. In the expanded configuration, the suturing clip is manipulated to recruit tissue of the body lumen by attachment thereto. Optionally, recruitment is by attachment of anchors positioned by the expanded arms to a predefined pattern, e.g., to a pattern complementary to a shape of the tissue being anchored in, and/or to a pattern which can be manipulated by relatively simple and/or stereotyped movements in order to achieve reliable attachment.

In some embodiments, anchors anchor in tissue with a success rate of less than complete anchoring, e.g., at least 75% anchoring, at least 80% anchoring, at least 85% anchoring, or another rate of anchoring success. In case one or more arms fail to anchor, the remaining anchors are potentially still sufficient to bring tissue of an aperture opening to a suitable closed configuration.

From the expanded configuration, the device is actuated to achieve closure. Closure, in some embodiments, comprises movement of the attachment points to a new configuration, by a motion which continues a direction of arm and/or anchor movement during expansion to the expanded configuration, resulting in an eversion of the initial collapsed delivery configuration. In some embodiments, the eversion comprises an arm portion such as an anchoring portion which is initially (for example) on a distal side of a core (base) of the suturing clip moves to a position on a proximal side of the core.

In some embodiments, additionally or alternatively, the eversion comprises an anchoring side of the arms which faces radially outward in the expanded anchoring state, but faced radially inward in the collapsed delivery state.

An aspect of some embodiments of the present disclosure relates to suturing clips configured for closure of an aperture in tissue to a closed band.

In some embodiments, suturing clips operate by moving a plurality of anchoring positions attached to a perimeter of the aperture from an open-aperture configuration to a closed-aperture configuration.

In some embodiments, movements of the plurality of anchoring positions comprise an interdigitation of anchoring positions moving from one side of the initial perimeter with anchoring positions moving from an opposite side of the initial perimeter. In some embodiments, the interdigitation comprises one or more anchors from one side of the initial perimeter (and/or a supporting member such as an arm that holds the anchors) crossing a geometrical line extending between two anchors from the other side of the initial perimeter.

In some embodiments, the closed band of the perimeter assumes a zigzag shape. For example, the local lateral extremes of the zigzag (the zigzag's angle vertices or "points") along one side of the zigzag correspond to anchors initially attached to a side of the aperture perimeter, and the local lateral extremes of the zigzag along the other side of the zigzag correspond to anchors initially attached to an opposite side of the aperture perimeter. In some embodiments, relative anchor positions relative to a central longitudinal axis of the zigzag are exchanged during closure, so that anchors from one side of the perimeter come to occupy positions on the opposite side of the axis upon closure. In some embodiments a zigzag shape comprises at least two segments extending between three anchoring sites, e.g., a chevron or "V" shape. In some embodiments, a zigzag shape comprises three or more segments (optionally, N segments, with N>2) extending between four or more anchoring sites (optionally, N+1 anchoring sites, each anchoring site corresponding to an anchor which is successfully anchored in tissue). In some embodiments, N+1 is a number of anchoring sites between 3 and 20. Optionally, vertices of the zigzag formed near each anchoring site are rounded.

A closed-aperture configuration provides a potential advantage for sealing and/or strengthening of the aperture closure over time, insofar as a relatively small extent of new endothelial tissue needs to be generated across the closed aperture compared, e.g., to a plug-type closure.

In some embodiments, movements of the plurality of anchoring positions comprise movement of at least one anchor radially outward from the initial perimeter, while other anchors move radially inward. By movement of the anchors, the perimeter is thereby both stretched in one direction, and collapsed in another direction, similar to the effect of flexible loop stretched between two oppositely-situated pulling forces.

An aspect of some embodiments of the present disclosure relates to the use of torsion bars (also referred to herein as "torque beams") as springs to provide actuating force to movements of flexible suturing clip elements such as arms and/or anchors mounted to the arms.

In some embodiments, torsion bars are provided by cutting into the material of a core and/or arm (e.g., laser cutting) a bar shape. Connected to the middle of the bar is a member of one side of the jointed element, and connected to the ends of the bar is a member of another side of the jointed element. The torsion bar has a relaxed state, setting an angle to which the joint will tend in the absence of external constraining forces. When the relaxed state is flat, the joint in the relaxed state will be flat (straight). When the relaxed state is twisted (e.g., because it was superelastically set to be twisted), the joint in the relaxed state will be torqued (e.g., bent outward, or in another direction). Forces that act to deform the joint from the relaxed state will be opposed by restorative forces. Torsion bars provide a potential advantage for storing a relatively large amount of potential energy in the spring for a given angular deformation (by twisting around a longitudinal axis), compared, for example, to deformation (deflection of the longitudinal axis) of a leaf spring of similar dimensions through the same angle.

In some embodiments, torsion bars enable manipulation of tissue between the expanded anchoring configuration and collapsed suturing configuration by a purely rotational movement. The movement is potentially without radial expansion. The movement is potentially along a direct, and potentially shortest route. This provides a potential advantage for reducing a likelihood of tissue disconnection from the anchors.

In some embodiments, torsion bars are angled at different angles relative to one another in order to provide arms of a suturing clip with a plurality of different corresponding angles of rotation. This is a potential advantage for increasing flexibility of configuration options in moving between a pre-movement configuration and a post-movement configuration of suturing clip components such as anchors.

An aspect of some embodiments of the present disclosure relates to shaping of an aperture in preparation for receiving a suturing clip. In some embodiments, an aperture spreader is actuated to engage with the sides of an aperture (such as an LAA ostium), in preparation for the advance of a suturing clip toward the aperture, expansion of the suturing clip, and/or anchoring of the suturing clip into tissue of the aperture.

Before explaining at least one embodiment of the present disclosure in detail, it is to be understood that the present disclosure is not necessarily limited in its application to the details of construction and the arrangement of the components and/or methods set forth in the following description and/or illustrated in the drawings. Features described in the current disclosure, including features of the invention, are capable of other embodiments or of being practiced or carried out in various ways.

Left Atrial Appendage Closure by Suturing Clips

Closure of the LAA

Reference is now made to FIG. 1A, which schematically illustrates a suturing clip 100 engaged to tissue within a LAA 1, according to some embodiments of the present disclosure.

Figures 1C, 1D:
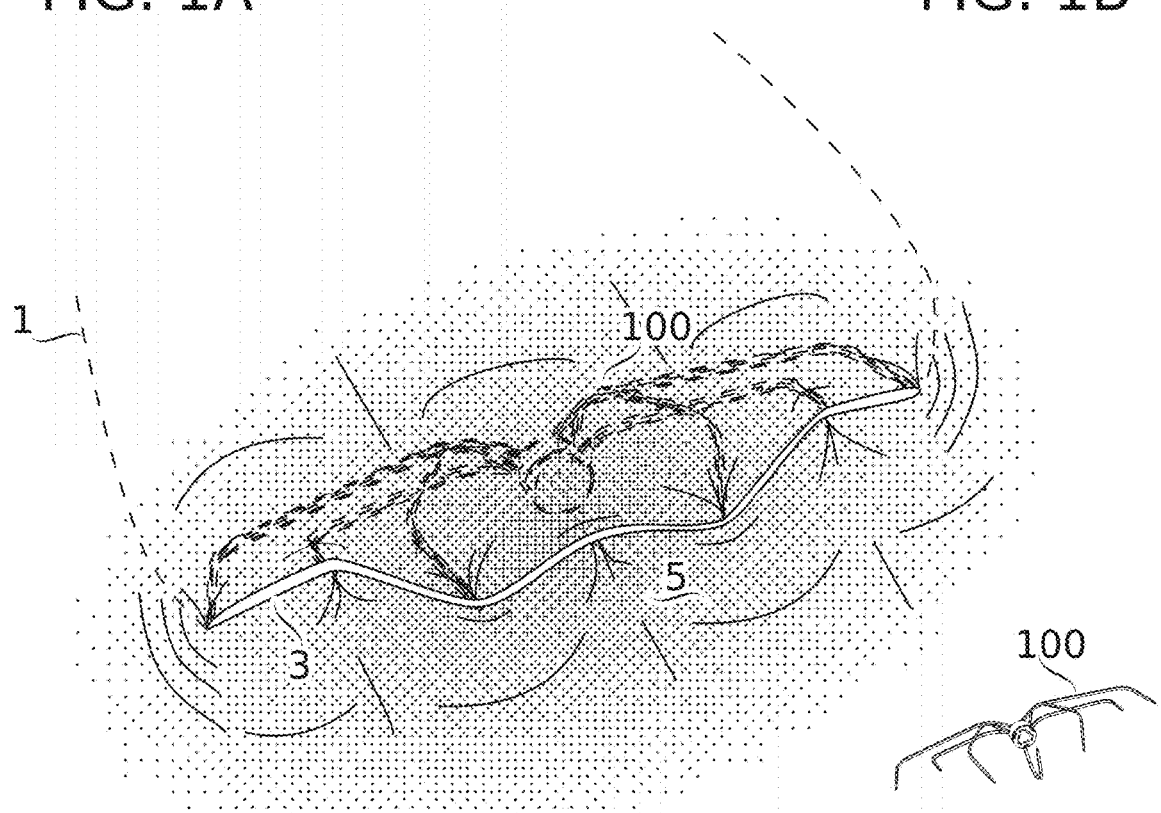
FIG. 1C schematically illustrates a suturing clip which has engaged tissue within an LAA and then undergone a conformational change to close an LAA ostium, according to some embodiments of the present disclosure.
FIG. 1D schematically illustrates the suturing clip of in the LAA-closing conformation of FIG. 1C, according to some embodiments of the present disclosure.

Reference is also made to FIG. 1B, which schematically illustrates the suturing clip 100 of FIG. 1A in an expanded configuration suitable for tissue engagement, according to some embodiments of the present disclosure. Further reference is made to FIG. 1C, which schematically illustrates a suturing clip 100 which has engaged tissue within an LAA 1 and then undergone a conformational change to close an LAA ostium 3, according to some embodiments of the present disclosure. Reference is also made to FIG. 1D, which schematically illustrates the suturing clip 100 of in the LAA-closing conformation of FIG. 1C, according to some embodiments of the present disclosure.

Suturing clip 100 is optionally configured according to any of a range of forms and designs, more particular examples of which include suturing clips 300, 350, 400, 500, and 800, described herein. These more particular examples vary from one another in features such as numbers of arms, specifics of arm shape, specifics of anchor shape, specifics of core design, and type of closure. Additionally or alternatively, embodiments of suturing clip 100 encompass any suitable arrangement of anchoring positions. For example, in the expanded anchoring configuration, the anchors are optionally arranged in a circular, elliptical, oval, split-curve (arranged along two or more perimeter sections), split-line (arranged along two or more line segments), and/or open-sided perimeter configuration. In the collapsed suturing configuration, for example, the anchors are optionally arranged in a circular (e.g., collapsed toward a common center), linear, zigzag, or another aperture closing configuration.

Generic features of a suturing clip 100 introduced in the descriptions of FIGS. 1A-1F should be understood to apply to any of the more particular embodiments herein, modified as explained in their more particular descriptions.

FIGS. 1A and 1C are drawn from a perspective on an atrial side of an LAA, looking at the LAA ostium 3, which is an opening in atrial wall 5 leading into LAA 1. FIGS. 1A and 1C show selected phases in the closure of LAA 1 using suturing clip 100.

FIG. 1A shows suturing clip 100 expanded within LAA 1, and FIG. 1B shows the same expanded suturing clip 100 without illustrating the surrounding tissue. Arms 104 of suturing clip 100 each deploy radially from their respective bases, where they connect to core 102. Anchors 106, positioned on respective terminal ends (i.e., ends opposite the ends attached to core 102; also referred to herein as "free ends") of arms 100, are configured to engage tissue from within LAA 1, for example by piercing, hooking, and/or pinching. In FIG. 1A, core 102 of suture clip 100 is connected to delivery system 110. Delivery system 110 comprises, in some embodiments, a catheter device, for example a percutaneous catheter device, of which distal catheter end 112 is illustrated. Previous to achieving the expanded position of FIG. 1A, suturing clip 100 was delivered by delivery system 110, e.g., enclosed within a lumen of distal catheter end 112 in a collapsed delivery configuration.

FIG. 1C shows suturing clip 100 in a collapsed suturing configuration, still engaged with tissue of LAA 1, and FIG. 1D shows the same collapsed suturing configuration of suturing clip 100 without illustrating the surrounding tissue. In the collapsed suturing configuration, suturing clip 100 draws the LAA ostium 3 closed from its position within LAA, creating a band of closure (optionally a zigzag band of closure as illustrated). LAA ostium 3 is closed potentially without any exposure of suturing clip 100 along an atrial side of atrial wall 5. For example, suturing clip 100 is entirely within the LAA 1 on the side of the closed LAA ostium 3, and/or suturing clip 100 is unexposed to the lumenal contents (e.g., blood) on the atrial side of atrial wall 5. This is a potential advantage for preventing device-induced thrombogenesis producing blood clots having access to the circulating blood pool. Attachment at the ostium 3 and/or adjacent to the ostium 3 is potentially advantageous over attachment at other positions within the LAA, insofar as tissue there may be thicker and/or stronger than tissue within the inner LAA.

Device Positioning in Preparation for LAA Closure

Reference is now made to FIG. 1E, which schematically illustrates a trans-septal approach insertion of a suturing clip 100 using a delivery system 110, according to some embodiments of the present disclosure.

Delivery system 110, in some embodiments, comprises a catheter overtube 111, distal catheter end 112, and delivery mount 113. Optionally, there is provided to delivery system 110 a stopper 118; configured, for example, as an inflatable balloon, expandable braid, and/or nitinol construction (for example, one or more flexible struts).

Also shown in FIG. 1E are schematic representations of atrium 4, including septal wall 9, pulmonary veins 6, mitral valve 7, LAA 1, and atrial wall 5 surrounding the ostium 3 of LAA 1.

Suturing clip 100 is shown in an expanded anchoring configuration, wherein arms 100 press anchors 106 outward to positions contacting tissue of the ostium 3 of the LAA, whereat the anchors 106 can be manipulated (e.g., by movement of the suturing clip via delivery mount 113) to anchor in the tissue.

It should be noted that in some embodiments stopper 118 is replaced by and/or used together with an expander, for example expander 1000 as described in relation to FIGS. 9A-10C.

Methods of LAA Closure

Operations During LAA Closure

Figure 1F:
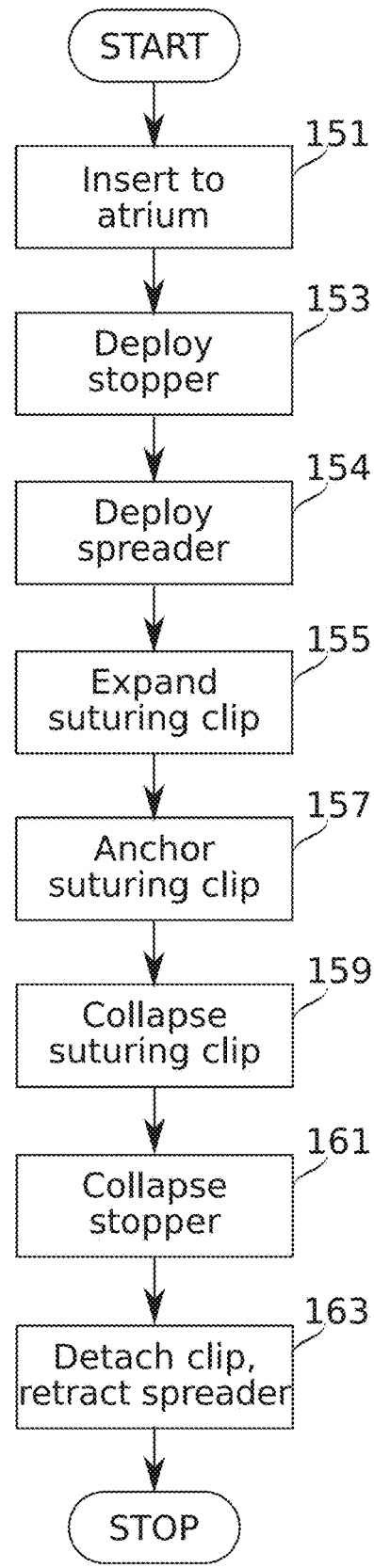
FIG. 1F is a schematic flowchart of a method of inserting of a suturing clip using a delivery system, according to some embodiments of the present disclosure.

Reference is now made to FIG. 1F, which is a schematic flowchart of a method of inserting of a suturing clip 100 using a delivery system 110, according to some embodiments of the present disclosure.

The flowchart of FIG. 1F begins after transseptal access is gained to an atrium, for example using a 0.35 inch guidewire. The punctured septum is dilated, and the sheath of the suturing clip 100 (catheter distal end 112) is introduced to the left atrium, and then positioned at the LAA ostium.

In some embodiments, deployment of a suturing clip 100 continues comprising the following operations:

At block 151, in some embodiments, insert the suturing clip 100 to the left atrium using deployment system 110.

At optional block 153, in some embodiments, stopper 118 is deployed and positioned against atrial wall 5. A tip 116 of deployment system 110 is positioned to pass into the ostium 3 of the LAA 1 when it is distally advanced. While stopper 118 is optional, it provides a potential advantage for ensuring that a correct (and preferably minimally required) insertion distance of suturing clip 100 is used during its deployment. Stopper 118 may also help to stabilize the LAA 1 and the delivery system 110 relative to one another during deployment.

At optional block 154, in some embodiments, spreader 1000 (described in relation to FIGS. 9A-10C) is deployed, for example as described in relation to FIGS. 9A-9F.

At block 155, in some embodiments, the suturing clip 100 is deployed to an expanded anchoring position; e.g. at least partially unsheathed by pushing forward on a control member of deployment system 110 to move forward portions of the system which hold and control the suturing clip (also referred to herein as the "internal system", and comprising delivery mount 113).

As suturing clip 100 advances out of distal catheter end 112, it changes shape from its collapsed delivery configuration to its expanded anchoring configuration. In some embodiments, expansion is automatic, as the arms 104 expand to assume their superelastically set shape.

At block 157, in some embodiments, the suturing clip 100 is anchored. In some embodiments, anchoring comprises pulling the suturing clip 100 backwards using the internal system, until it anchors into tissue of the ostium wall via anchors 106 positioned on the ends of arms 104. Optionally, a position of suturing clip 100, its arms 104 and/or its anchors 106 is verified before and/or after anchoring, for example by use of imaging observation (e.g., ultrasound imaging and/or fluoroscopy). Optionally, anchoring is verified by a "tug test", comprising one or both of detecting resistance to retraction, and viewing movement under imaging observation. Optionally, suturing clip 100 is provided with one or more radiopaque markers to assist in visualization of the anchors 106, arms 104, and/or core 102 of the device. For example, anchors 106 or another part of suturing clip 100 comprise an alloy more radiopaque than nitinol (e.g., a radiopaque marker comprising gold, tungsten, or another material). In some embodiments, delivery system 110 comprises a radiopaque marker, positioned to identify, for example, a portion of delivery mount 113.

At block 159, in some embodiments, the suturing clip is collapsed to its collapsed suturing configuration. Developing sufficient closing force from the suturing clip 100 is a potential challenge. A typical catheter inner lumen diameter, for example, is about 3-5 mm, within which the collapsed delivery configuration of the suturing clip is positioned. The diameter of the LAA may be approximately 30 mm, potentially creating a situation of mechanical disadvantage, since by the principles of leverage, forces exerted tend to reduce as distance from the fulcrum increases.

Closing force, in some embodiments, is exerted by using the internal system to pull backward on a closure disk 120 (e.g., as described in relation to FIGS. 2N-2P, herein). In some embodiments, a closure disk 120 operates by sliding along a plurality of arms from a base region of the arms and toward an anchoring end of the arms. The closure disk is connected to the arms (e.g., via one or more apertures) so that as it moves, it changes radial expansion of the arms 104, and thereby collapses the arrangement of anchors 106 into their collapsed suturing configuration, drawing anchoring tissue of the ostium 3 along with them. Closure disks are also referred to herein as closure "rings". Examples and additional description of closure disks, their functioning and their operation are also described, for example, in relation to FIGS. 2M-4H, herein. Closure disks provide a potential advantage by bringing the fulcrum of mechanical leverage closer to the anchoring sites at which the tissue closure is formed.

Optionally, the roles of superelasticity and the disk are reversed. For example, the suturing clip, in some embodiments, is superelastically set to assume the closed position, and the disk initially set in a more proximal position. Movement of the disk forced distally potentially also forces the suturing clip to open and assume the expanded anchoring state, e.g., by approaching a distal part of the suturing clip whereat the arms come together within a radius smaller than the apertures in the disk through which they pass. Upon relaxation of force on the disk, the arms tend to close, urging the disk proximally again. Optionally, the disk is pulled proximally again. It is noted that the self-expanding configuration of such disk-controlled devices is potentially more mobile than a corresponding self-collapsing configuration, due to differences in size constraints.

In some embodiments, another method of developing force for collapse to the collapsed suturing configuration is used; for example an everting-type closure, wherein the arms are themselves resiliently biased to continue on toward closure after passing through a more expanded configuration. In such configurations, the collapsed delivery configuration of arms 104 as contained by delivery system 110 may orient them to extending from a proximal side near core 102 distally toward their free anchoring ends. It may be noted that the design used as an example in FIGS. 1A-1D to illustrate certain generic features of a suturing clip 100 happens to undergo everting-type closure. The design used as an example in FIG. 1E of certain generic features of a suturing clip 100 and its delivery system 110 happens to undergo what is referred to herein as reverting-type closure. Features related to the specifics of these closure types (as well as other details of the specific designs) are discussed in relation to the several more particular embodiments of the device, and, for example, in relation to FIGS. 2A-2I, herein. In an everting design, leverage is potentially increased in part by the collapse of the arm itself to a shorter leverage distance due to curvatures along the length of the arm. Moreover, a portion of the force generated for closure is optionally created through use of a torsion bar feature (also referred to herein as a "torque beam") in the design of the suturing clip 100. A torsion bar is a spring design (exerting rotational force through a plane transverse to a longitudinal axis of the bar or beam) which can potentially exert relatively high force compared to a leaf spring (e.g., flexible arm, exerting rotational force through a plane passing along a longitudinal axis of the arm) of the same general size and material.

In some embodiments, closure is verified; for example by fluoroscopy and/or ultrasound (echocardiography). In some embodiments, closure is verified by the tracking of dye from an injection made within or outside the LAA.

In some embodiments, closure is followed by suction and/or an injection of material (e.g., saline) to remove and/or displace blood remaining the LAA. This potentially helps reduce a possibility of a blood clot forming even within the closed-off pocket of the LAA formed by the suturing clip.

At optional block 161, in some embodiments, stopper 118 (if used) is re-collapsed.

At block 163, in some embodiments, the delivery system 110 is detached from the suturing clip 100 and removed from the body. Optionally, detachment occurs as part of the collapse to a suturing configuration of suturing clip 100, and/or immediately thereafter.

Optionally, operations of the various blocks are returned to in reverse during deployment, for example in order to reposition the suturing clip 100 based, for example, on fluoroscopic observations (e.g., spread of injected dye), and/or other observations and/or feedback.

Closure of an Aperture from a Side Opposite the Approach Side

Figure 1G:
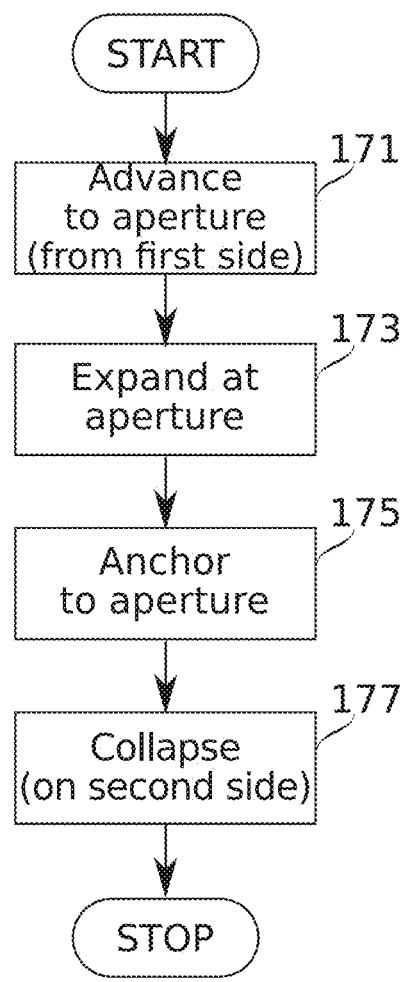
FIG. 1G is a schematic flowchart of closure of a body lumen aperture by a suturing clip which closes the aperture from a side of the closure opposite a side from which the suturing clip is introduced, according to some embodiments of the present disclosure.

Reference is now made to FIG. 1G, which is a schematic flowchart of closure of a body lumen aperture by a suturing clip 100 which closes the aperture from a side of the closure opposite a side from which the suturing clip is introduced, according to some embodiments of the present disclosure.

At block 171, in some embodiments, the suturing clip 100 is advanced from a first side of a body lumen aperture (e.g., an ostium 3 of an LAA 1) toward a second side of the body lumen aperture.

At block 173, in some embodiments, the suturing clip 100 is expanded with at least a portion of it positioned on the second side of the body lumen aperture.

At block 175, in some embodiments, the suturing clip 100 is anchored into the body lumen aperture (e.g., using anchors positioned on the portion of the suturing clip 100 on the second side of the body lumen aperture).

At block 177, in some embodiments, the suturing clip 100 is collapsed to close the body lumen aperture, with the suturing clip 100 remaining on the first side of the body lumen aperture.

Clip Configuration Changes During LAA Closure

Reference is now made to FIGS. 2A-2I, which schematically illustrate stages in the deployment of a suturing clip 100, according to some embodiments of the present disclosure. Herein, the reference characters "100" are used in descriptions of suturing clips in general, with certain more particular embodiments being given their own reference characters identifying them as species of the genus, and/or described with reference to their particular characteristics.

Figure 2A:
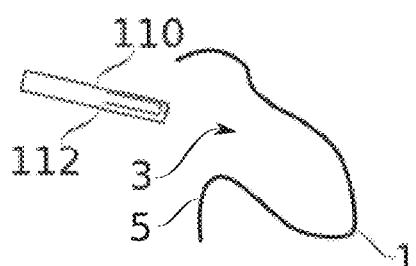
FIGS. 2A-2I schematically illustrate stages in the deployment of a suturing clip, according to some embodiments of the present disclosure.

FIG. 2A, in some embodiments, represents the approach of a delivery system 110 including a distal catheter end 112 toward an ostium 3 of a left atrial appendage 1 in the atrial wall 5 of a heart atrium.

Figure 2B:
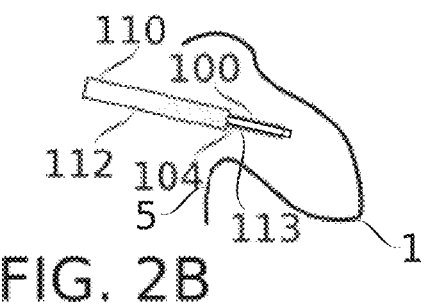
Figure 2F:
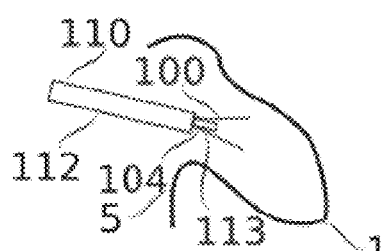

FIGS. 2B and 2F, in some embodiments, represent partial unsheathing of suturing clip 100 by actuation of delivery system 110. Unsheathing comprises, for example, retraction proximally of distal catheter end 112 from delivery mount 113, and/or extrusion distally of delivery mount 113 from catheter end 112. In the example of FIG. 2B, suturing clip 100 is packaged with core 102 on a distal side of the collapsed delivery configuration, and anchoring ends of arms 104 on a proximal side of the collapsed delivery configuration. In the example of FIG. 2F, the configuration is reversed distal-proximally, for example, as described in relation to FIGS. 5A-8G, herein. Anchoring ends on the more distal side is also the configuration shown in FIGS. 1A-1D.

Figure 2C:
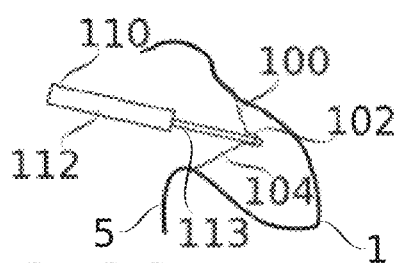
Figure 2G:
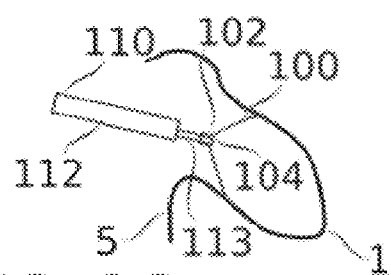

FIGS. 2C and 2G, in some embodiments, represent expansion of arms 104 of suturing clip 100 radially away from core 102 (relative to the positions of FIGS. 2B and 2F, respectively); and their initial engagement (via anchors 106, not illustrated) with a lumenal side of tissue within LAA 1. Expansion of arms 104, in some embodiments, comprises a superelastic configuration change due to arms 100 being set, when unconstrained, to expand as shown. Additionally or alternatively, a separately actuated mechanism forces expansion of arms 104.

Comparing FIGS. 2C and 2G, it may be seen that there is a potential advantage of lowered initial insertion distance for an everting suturing clip as in FIG. 2G. Lowered insertion distance potentially reduces a risk of LAA perforation. This risk occurs, for example, since the LAA interior comprises relatively thin and/or fragile tissue compared to the muscular wall of the rest of the heart, and/or because of potential difficulties in obtaining a clear view of the complicated 3-D shape of the LAA. In contrast to inserting a whole suturing clip 100 in a still-collapsed (and thus longitudinally maximally extended) configuration (and then expanding), an everting-type closure suturing clip 100 can be gradually expanded as it advances distally, with the most-expanded part also being its distal-most portion. This potentially reduces a risk of perforation by elements positioned on the relatively stiff central axis of the delivery system, since these elements are not distal-most during an important stage of initial deployment, and optionally are not themselves inserted into the LAA during deployment, or inserted to a minimal degree. Insofar as the suturing clip 100 itself is "self-driving", it is the case in some embodiments that it need only be engaged at a proximal side of ostium 3 of LAA 1, and not actively inserted further than this. Once collapse to the collapsed suturing configuration is allowed to proceed, it draws itself into the LAA, to a distance limited by the previously established anchoring fixation. It should be noted that non- or minimal-insertion deployment also potentially reduces a chance of dislodging a potentially pre-existing thrombus during the deployment procedure. After anchoring, there remains some protection given from potential perforation events, since the anchoring itself controls a maximal distance of delivery system advance (e.g., prevents further advancing).

Figure 2D:
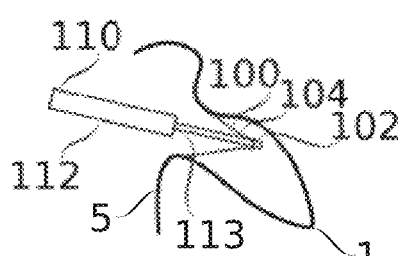
Figure 2H:
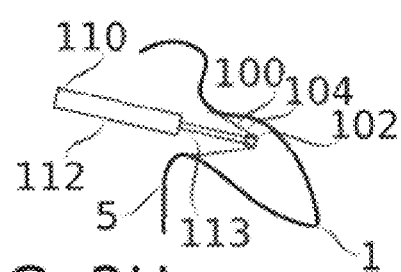

FIGS. 2D and 2H, in some embodiments, each represent an intermediate stage of closure of arms 104 toward a collapsed suturing configuration. Different actuation mechanisms and/or shape transitions may be used to complete the closure of ostium 3. In FIG. 2D, for example, arms 104 are re-collapsing by being forced back along the same direction from which they expanded. Herein, this is also referred to as a "reverting"-type closure. Optionally, this is accomplished by movement of a closure disk 320 (FIG. 3C) that slides proximally along arms 104, forcing them closed. In some embodiments, additionally or alternatively, resilient elasticity of arms 104 is used to provide force for closure.

Optionally, closure comprises a continued conformational change of arms 104, for example as shown in FIG. 2H. Herein, this type of closure is also referred to as an "everting" closure, wherein initially distally-pointing arms 104 (e.g., oriented as in FIG. 2F) continue to rotate past their most-expanded state, reversing their proximal-distal orientation relative to core 102 to point proximally. The suturing clip 100 of FIGS. 1A-1D also represents an "everting"-type suturing clip. A potential advantage of everting-type closure is a lowered distance of penetration into the LAA during insertion, reducing one or more of a risk of perforation and a risk of dislodging a pre-existing thrombus.

Figure 2E:
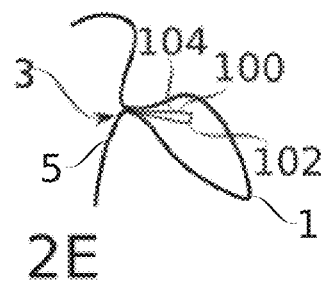
Figure 2I:
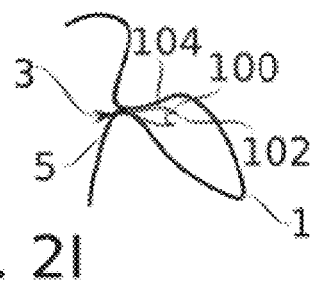

FIGS. 2E and 2I, in some embodiments, each represent a final stage of closure, wherein the arms 104 have reached a fully closed collapsed suturing configuration. LAA ostium 3 is now closed. Delivery system 110 is detached, and suturing clip 100 remains attached to lumenal-side tissue of LAA 1, and sequestered within LAA. Insofar as suturing clip 100 is so-sequestered, it is prevented from acting as a center of thrombogenesis for blood clots which could enter the general circulation. Potentially, the sutured sides of the ostium 3 of LAA 1 will gradually grow together, preventing reopening of LAA 1.

Anchor Movements During LAA Closure

Figure 2J:
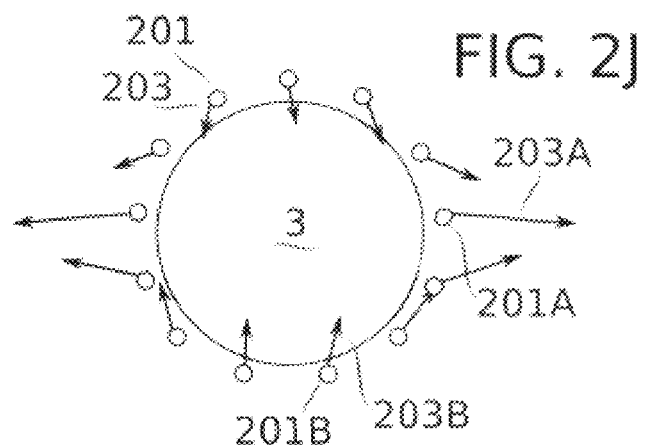
FIGS. 2J-2L schematically illustrate movements of anchoring positions over the course of a transition of a suturing clip between a deployed- and-anchored configuration, and a collapsed suturing configuration, according to some embodiments of the present disclosure.
Figure 2K:
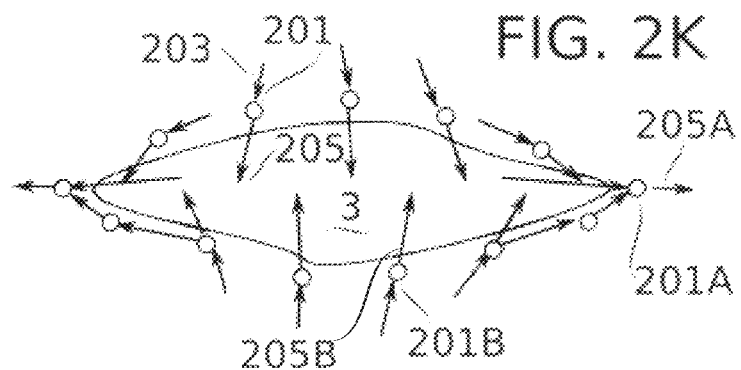
Figure 2L:
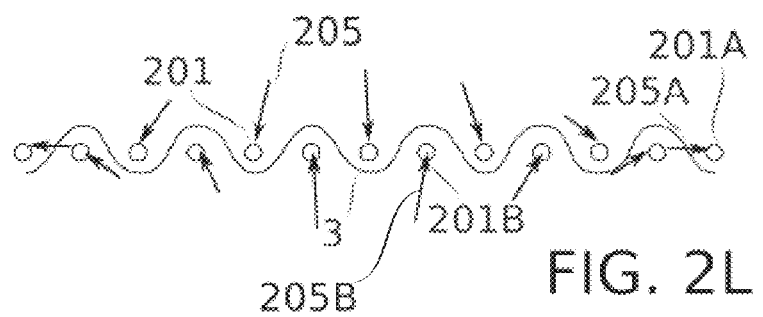

Reference is now made to FIGS. 2J-2L, which schematically illustrate movements 203, 205, 203A, 203B, 205A, 205B of anchoring positions 201, 201A, 201B over the course of a transition of a suturing clip 100 between a deployed- and-anchored configuration, and a collapsed suturing configuration, according to some embodiments of the present disclosure. The movements are shown as they would be viewed from a direction looking into the LAA through the aperture of ostium 3.

The movements shown optionally apply to either or both of everting and reverting suturing clips 100. In FIG. 2J, anchoring positions 201 are initially arranged around an interior circumference of ostium 3. Herein the reference characters 201 refer generically to anchoring positions (of which one particular instance is labeled), and the reference characters for anchoring position 201A refer to a particularly labeled instance of an anchoring position 201.

As a suturing clip 100 collapses (FIG. 2K), the anchoring ends of each arm 104 move in different directions within the viewing plane. Arrows 203, 205 (as identified generically) each point in a different direction, indicating the position to which each anchoring position 201 moves between the configurations of FIG. 2J and the positions of FIG. 2K and then FIG. 2L.

It is noted in particular that there is motion of some anchoring positions (e.g., anchoring position 201A in directions 203A and then 205A) radially outward, while other anchoring positions (e.g., anchoring position 201B in directions 203B and then 205B) move generally radially inward. There is, however, a convergence in common to a shared suturing line. As a result, suturing clip 100 gradually draws ostium 3 into a new, nearly linear shape which retains most of the perimeter length of original ostium 3 (e.g., at least 50%, 70%, 80%, 90%, or 100% of the original perimeter length). Herein, the term "laterally-displacing collapse" is used to refer to collapsing movements of anchoring positions 201, arms 104, anchors 106, and/or other elements of a suturing clip 100, which act to stretch an aperture in one direction (i.e., laterally) while collapsing it in another.

A pattern of laterally-displacing collapse is seen, for example, in the embodiments of FIG. 5A-8G, and in another form in the embodiments of FIGS. 4A-4F. While not every embodiment of the current disclosure shows laterally-displacing collapse (e.g., the embodiments of FIGS. 3A-3D), laterally-displacing collapse it is a potential advantage to help reduce stresses due to "puckering" or "gathering" which could occur when all anchoring positions are drawn toward a common radial center.

FIG. 2L shows the anchoring positions 201 in the collapsed suturing configuration. The actual collapsed suturing configuration depends on a balance between forces placed on anchoring positions 201 urge them toward the same line—or even toward positions past the same line—and forces that resist this motion. In some embodiments, the result is a wavy ("clam shell") or other irregular pattern along the lip of ostium 3. For example, tissue near to an anchoring position 201 tends to press further inward, while tissue further away from an anchoring position tends to give way to this pressure. To this extent, mechanical properties of the tissue itself become part of the seal created by the suturing clip 100 at the site of the ostium 3. In the collapsed suturing configuration, for example, the anchors 106 are optionally arranged in any suitable configuration for closure, e.g., a circular (e.g., collapsed toward a common center), linear, zigzag, or another aperture-closing configuration.

Delivery Packaging and Closure Ring Operation

Reference is now made to FIGS. 2M-2P, which illustrate details of interactions between a delivery system 110 and a suturing clip 100, according to some embodiments of the present disclosure.

FIG. 2M shows a delivery system 110 in a pre-deployment configuration. Suturing clip 100 is held within distal catheter end 112 in a collapsed delivery configuration. Optionally, distal catheter end 112 comprises a sheath of tubing at least long enough to fit over collapsed suturing clip 100. It may be as long as the whole catheter, or it may comprise a shorter segment which is actuated to withdraw by a control member such as a rod or wire controlled from a proximal side of the delivery system 110, outside the body. Optionally, catheter distal tip 116 comprises an atraumatic tip, for example, constructed of a suitable polymer material.

In FIG. 2N, distal catheter end 112 has been rendered transparent, in order to show details of suturing clip 100 in its collapsed delivery configuration. In the example shown, arms 104 are held flattened against delivery mount 113, constrained by being held within distal catheter end 112. Anchors 106 occupy a proximal side of the arms 104 in this configuration, and core 102 occupies a distal side of the arms 104. In some embodiments, closure disk 120 is initially positioned near the base of the arms at core 102. In this position, closure disk 120 exerts little or no control over the expansion of arms 104 when they are extruded from catheter distal end 120 (and/or catheter distal end 120 is withdrawn), for example as shown in FIG. 2O.

In FIG. 2O, the arms 104 are shown expanded, positioning the anchors 106 in a radially symmetrical pattern. Optionally, arms 104 expand to place anchors 106 in another configuration, for example, a pattern corresponding to portions of a perimeter of the ostium 3 of an LAA. Arms 104 expand enough to bring anchors 106 in contact with tissue. Arms 104 are potentially prevented from fully expanding to assume their superelastically set shape by this contact, and in this condition forces developed in the arms 104 themselves may assist in achieving tissue anchoring. Optionally, the suturing clip 100 is manipulated (e.g., pulled proximally and/or rotated using delivery mount 113) to achieve tissue anchoring.

In FIG. 2P, suturing clip 100 is shown closed again, this time to its collapsed suturing configuration. In this case, the collapse comprises a proximal movement of closure disk 120 relative to core 102. This proximal movement may be obtained using delivery mount 113, since once anchors 106 are anchored to tissue, the rest of the device will tend to resist distal movement.

Optionally, the internal system comprises a separately controllable member for moving closure disk 120, while delivery mount 113 remains in position. This provides a potential advantage, for example, for reversibility of deployment. Using such a control configuration, suturing clip 100 is optionally completely re-collapsed so that it can be once again withdrawn into catheter distal end 112.

Suturing Clip with Radial Arms and Closure Disk

Figure 3A:
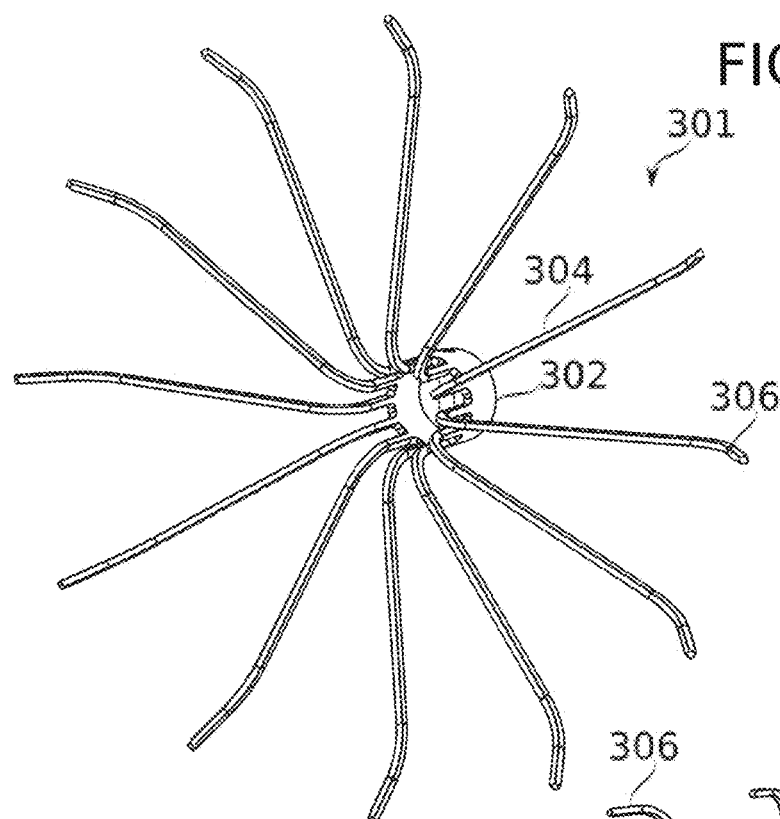
FIG. 3A schematically illustrates an expanded configuration of a reverting core-and-arm assembly of a suturing clip, according to some embodiments of the present disclosure.
Figure 3B:
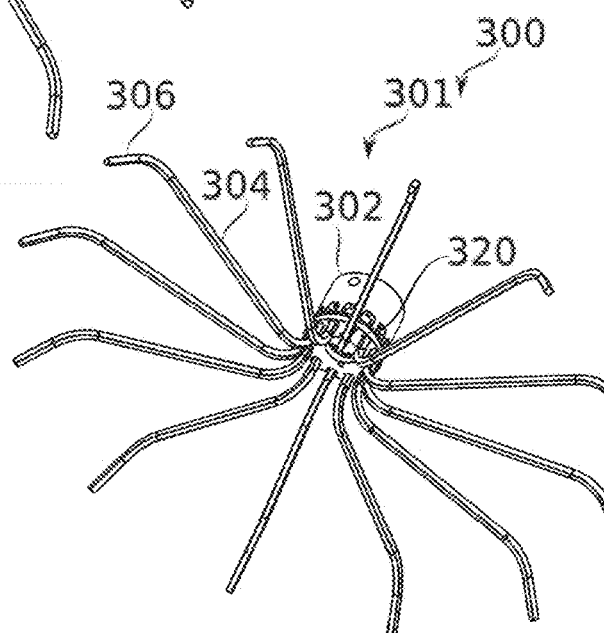
FIG. 3B schematically illustrates a suturing clip an expanded configuration, including closure disk, according to some embodiments of the present disclosure.

Reference is now made to FIG. 3A, which schematically illustrates an expanded configuration of a reverting core-and-arm assembly 301 of a suturing clip 300, according to some embodiments of the present disclosure. Reference is also made to FIG. 3B, which schematically illustrates suturing clip 300 an expanded configuration, including closure disk 320, according to some embodiments of the present disclosure. Further reference is made to FIG. 3C, which schematically illustrates suturing clip 300 in a re-collapsed suturing configuration, collapsed by movement of closure disk 320, according to some embodiments of the present disclosure, and additional reference is made to FIG. 3D, which schematically illustrates suturing closure disk 320, according to some embodiments of the present disclosure. Suturing clip 300 is an example of a reverting-type suturing clip 100.

In some embodiments, a suturing clip 300 comprises a core-and-arm assembly 301 (FIG. 3A) and a closure disk 320 (FIG. 2C), assembled together so that arms 304 of core-and-arm assembly 301 pass through apertures 321 of closure disk 320. Prior to delivery, arms 304 are collapsed and held in place, e.g., by a surrounding lumen of a portion of delivery system 110. As the arms 304 are released from this constraint, they expand toward the arm position shown in FIG. 3B. Constraining ring 320 at this stage is positioned at the base of arms 304, near core 302. The expanded device is manipulated within an LAA 1 so that anchors 306 anchor (fasten) into tissue. Details of anchors 306 are suppressed in the schematic drawing, but can be of any design suitable for piercing and/or gripping tissue, for example spiked anchor 413 of FIG. 4A, spiked anchor 806 of FIG. 8A, and/or barbed anchor 506 of FIG. 5A.

Once the anchors are attached, closure disk 320 is moved from its initial position near core 302 toward the anchoring ends of the arms 304. This acts to pull the arms 304 inward, so that their tips converge. Accordingly, tissue surrounding a closure created by a device of this design tends to form a radial "pucker" or surgical purse-string result, as tissue is forced into a smaller region than its natural perimeter allows. Mechanical strength to do so is obtained from the increased stiffness of the arms as they shorten, and the strength and mechanical advantage of closure disk 320.

Optionally, a single deployment member acts both to carry suturing clip 300 into position and to pull closure disk proximally, since the force of anchoring will tend to resist the force of pulling the single deployment member proximally (this is further described, for example, in relation to FIGS. 4E-4F and suturing clip 400).

Alternatively, movement of closure disk 320 relative to base 302 is optionally obtained by mounting the whole suturing clip 300 to a first deployment member of delivery system 110, and then using a second deployment member to pull closure disk proximally while the rest of the device is held in place by the first deployment member.

In some embodiments, closure disk 320 comprises a locking aperture 322 through which the first and optionally the second deployment member of delivery system 110 extend. In some embodiments, cutouts 323 of locking aperture 322 provide a passage to which a deployment member can be rotated to allow withdrawal after the device achieves closure.

Figure 3D:
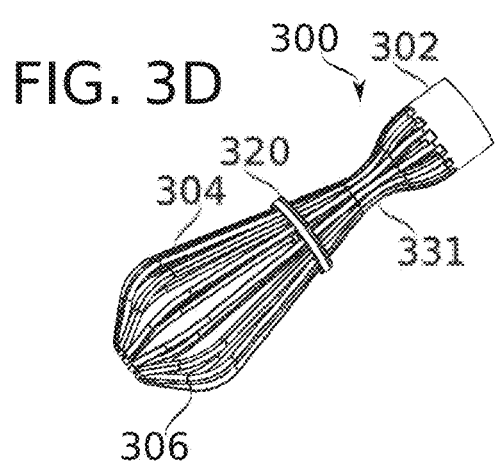
FIG. 3D schematically illustrates a suturing closure disk, according to some embodiments of the present disclosure.
Figure 3C:
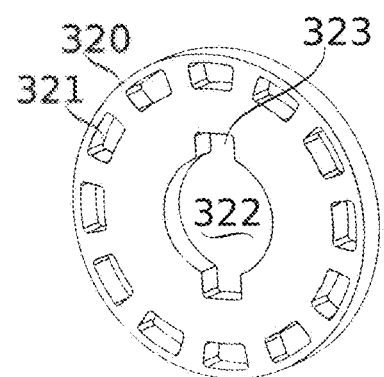
FIG. 3C schematically illustrates a suturing clip in a re-collapsed suturing configuration, collapsed by movement of closure disk, according to some embodiments of the present disclosure.
Figure 3E:
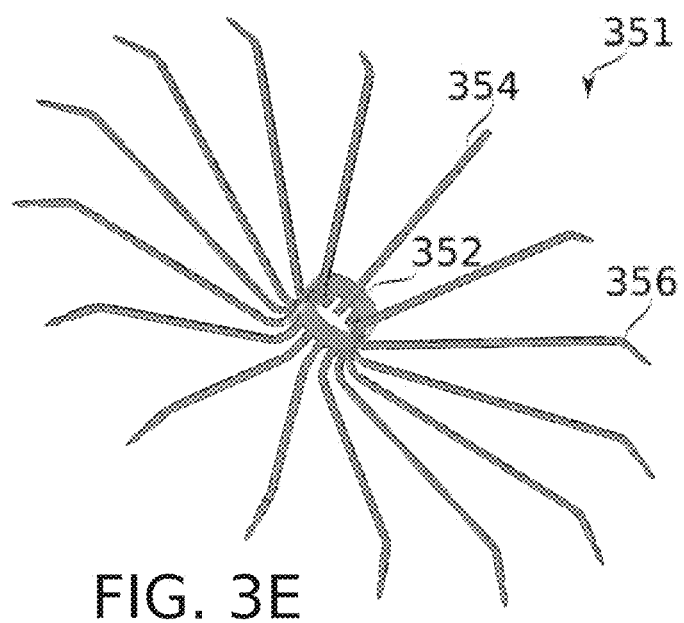
FIG. 3E schematically illustrates an expanded configuration of a reverting core-and-arm assembly of a suturing clip, according to some embodiments of the present disclosure.
Figure 3G:
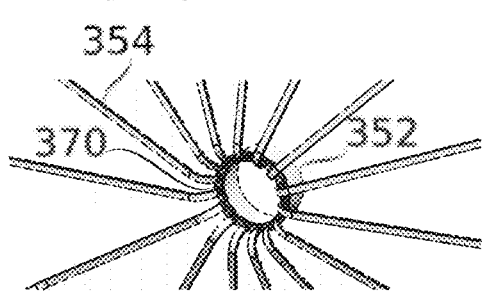
FIGS. 3F-3G schematically illustrate a suturing clip an expanded configuration, including closure disk, according to some embodiments of the present disclosure.
Figure 3F:
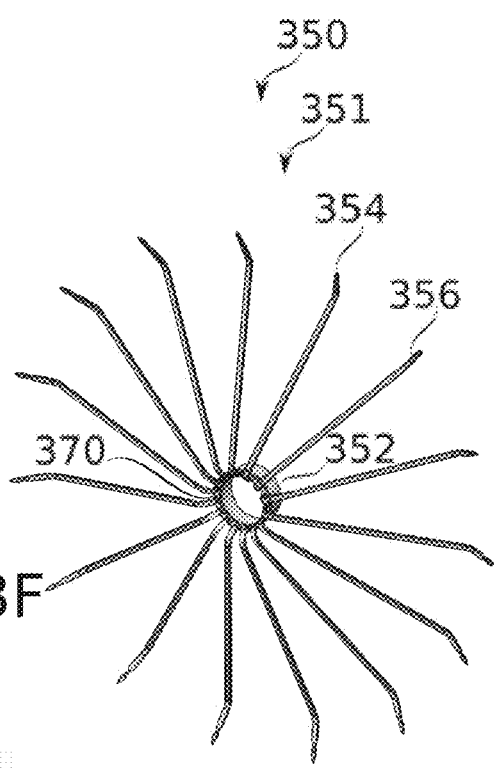

Reference is now made to FIG. 3E, which schematically illustrates an expanded configuration of a reverting core-and-arm assembly 351 of a suturing clip 350, according to some embodiments of the present disclosure. Reference is also made to FIGS. 3F-3G, which schematically illustrate suturing clip 350 an expanded configuration, including closure disk 370, according to some embodiments of the present disclosure. Further reference is made to FIG. 3H, which schematically illustrates suturing clip 350 in a re-collapsed suturing configuration, collapsed by movement of closure disk 370, according to some embodiments of the present disclosure, and additional reference is made to FIG. 3I, which schematically illustrates suturing closure disk 370, according to some embodiments of the present disclosure. Suturing clip 350 is an example of a reverting-type suturing clip 100.

In terms of its use and mechanisms of action, suturing clip 350 is of the same family of reverting-type closure designs as suturing clip 300, with, e.g., a different number of arms, a different closed shape to the arms, and an explicitly illustrated shape (barbed) for anchors 356. It may be noted that arms 304 collapse at a place along their length more nearly to a radial center (e.g., at pinch 331 FIG. 3D) than the arms of suturing clip 350. This more radially pinched shape provides a potential advantage for generating additional inward force during closure, albeit closure disk 320 potentially provides the principle fulcrum once closure is completed. The pinched shape may also allow a different range of options for angles at which anchors 106 (of which, e.g., anchors 306, 356 are particular examples) contact tissue.

Suturing Clip with Branched Arms and Closure Disk

Figure 4A:
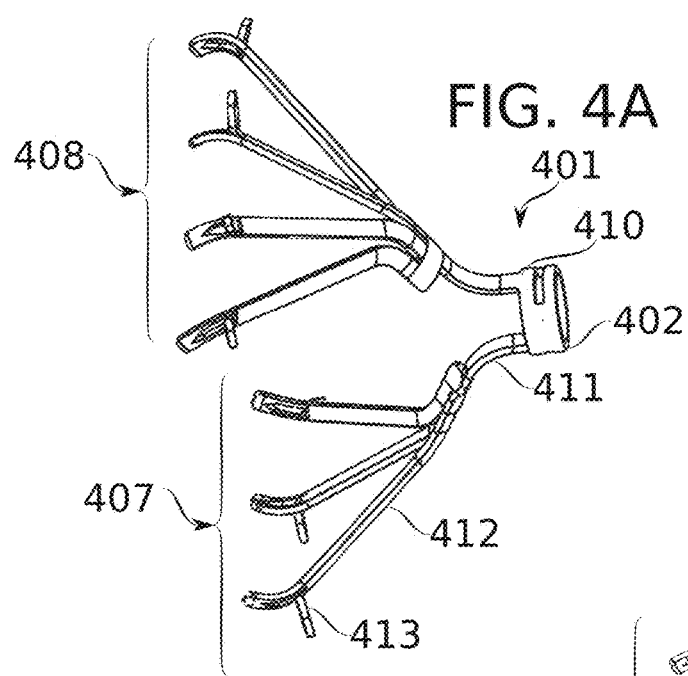
FIG. 4A schematically illustrate an expanded configuration of a core-and-arm assembly of a suturing clip, according to some embodiments of the present disclosure.
Figure 4B:
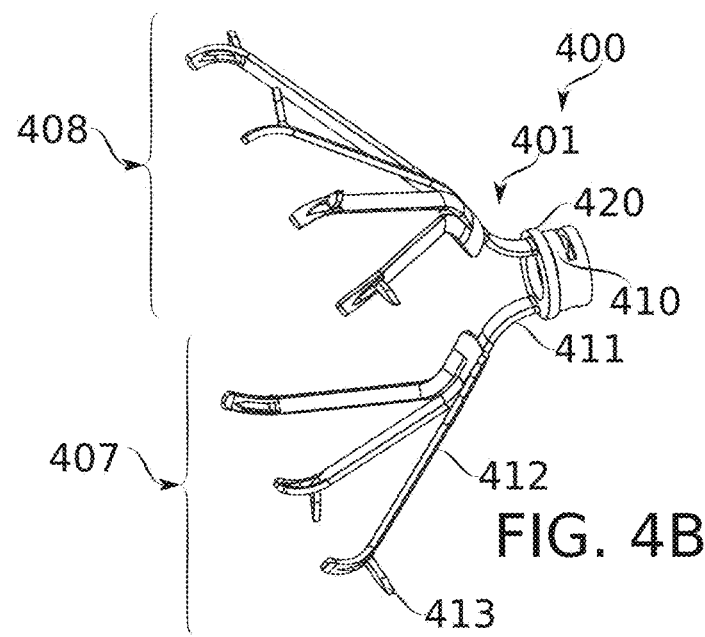
FIG. 4B schematically illustrates a suturing clip an expanded configuration, including closure disk, according to some embodiments of the present disclosure.

Reference is now made to FIG. 4A, which schematically illustrate an expanded configuration of a core-and-arm assembly 401 of a suturing clip 400, according to some embodiments of the present disclosure. Reference is also made to FIG. 4B, which schematically illustrates suturing clip 400 an expanded configuration, including closure disk 420, according to some embodiments of the present disclosure. Further reference is made to FIG. 4C, which schematically illustrates suturing closure disk 420, according to some embodiments of the present disclosure. Suturing clip 400 is an example of a reverting-type suturing clip 100.

Like suturing clip 300, suturing clip 400 comprises a core-and-arm assembly 401 and a closure disk 420, wherein movement of closure disk 420 away from the core 402 and toward the tips of arm subassemblies 408, 407 brings about reverting collapse of the arm subassemblies 407, 408, which otherwise tend bend and to expand the suturing clip radially upon release from enclosure during delivery.

Each of the arm subassemblies 407, 408 comprises a plurality of arms 412, individually equipped with anchors 413 of the spike design shown, and/or of another anchor design. Arms 412 of each arm subassembly 407, 408 are biased to expand so that they spread their anchoring ends to define a partial perimeter. The partial perimeter may be, for example, linear, or with only a slight curvature (this is shown, for example, in the distal-to-proximal view of FIG. 4G). Arm assembly trunk 411, for its part, is biased to bend when unconstrained so that the two sets of arms take up positions on either side of the ostium of the LAA.

Closure of suturing clip 300, in some embodiments, comprises constraining the arm assembly trunks 411 to revert to more-straightened positions (e.g., by movement of closure disk 420 to slide along the arm assembly trunks 411). The individual arms 412 are optionally allowed to remain spread out, so that the closure of the LAA is spread out into a flattened configuration.

Further reference is now made to FIGS. 4D-4H, which show deployment of suturing clip 400 under control of a deployment system 410, including deployment member 415, according to some embodiments of the present disclosure. In some embodiments, deployment member 415 is interconnected to the device through aperture 422 of closure disk 420. In some embodiments, protrusions on deployment member 415 interlock with a portion of core 402 (e.g., protrude into apertures 410). If initially attached to core 402, release of deployment 415 may be achieved, for example, by rotation of deployment member 415.

Once suturing clip 400 is anchored, pulling deployment member 415 proximally moves closure disk 420 proximally along with it. As shown in FIGS. 4F (from the side) and 4G (looking proximally), arm subassemblies 407, 408 are brought together by this movement. Optionally, they are shaped so that in a completely actuated position arm subassemblies 407, 408 interdigitate. Interdigitation optionally comprises movements of portions of the arms 412 on arm subassembly 407 from a first side of the arms 412 of arm subassembly 408 to a second side of the arms 412 of arm subassembly 408. Connection of the anchors 406 to tissue may restrict the degree of interdigitation. The resulting closure may resemble the zigzag closure band of the ostium 3 in FIG. 1C, for example; extending alternately between arms 412 of arm subassembly 408 and of arm subassembly 407.

Full release of deployment member 415 is optionally performed by partial rotation, stronger pulling, actuation of unlocking members on deployment 415, and/or another method.

It should be noted that stages of deployment (for this and optionally any other embodiment of the present disclosure) are optionally fully- or partially-reversible. For suturing clip 400, for example, this may be achieved by reconnecting deployment member 415 and suturing clip 400, restoring closure disk 420 to its original position, and/or moving the re-expanded suturing clip 400 to extract it from its anchored position. Reversibility is a potential advantage during implantation (e.g., to allow adjustments), and/or to facilitate an option for emergency retrieval of the device.

Suturing Clip with Self-Collapsing, Radial Arms

Reference is now made to FIGS. 5A-5D, which schematically illustrate parts of an everting suturing clip 500, according to some embodiments of the present disclosure. Suturing clip 500 is an example of an everting-type suturing clip 100.

In some embodiments, a suturing clip 500 comprises a plurality of arm subassemblies 501A, 501B, 501C (collectively, arm subassemblies 501A-501C) which each separately provide portions of both the core (e.g., core portions 502A, 502B, 502C, referred to collectively as cores 502A-502C and/or equivalently in a unit as core 502) and the arms (e.g., arms 504A, 504B, 504C, 504D, 504E, and 504F; referred to collectively and equivalently as arms 504A-504F and/or arms 504). Arms 504A-504F are optionally of a plurality of individual designs, having lengths, orientations, and/or bending behaviors which function collectively to achieve a targeted closure configuration. Arms 504A-504F are each terminated by an anchor 506; for example of the barbed anchor type shown, and/or of another design and/or type. In some embodiments a portion of the bending behavior of an arm 504A-504F is determined by the orientation and preset (i.e., super-elastically set) rotation of a torsion bar by which it is attached to the core, for example, one of torsion bars 530, 532, 534 (also referred to collectively as torsion bars 530), which are optionally oriented to rotate in different planes for different arms 504A-504F.

In some embodiments, the arm subassemblies 501A-501C are attached to one another via connecting disk 520, e.g., by insertion of hooks 540 of each arm subassembly 501A-501C into apertures 521 of connecting disk 520. Optionally, connecting disk 520 is secured to arm subassemblies 501A-501C by glue and/or welding. Optionally, connecting disk 520 is of titanium or another material (e.g., another biocompatible alloy such as stainless steel), and the various arm subassemblies 501A-501C are formed from a superelastic alloy such as nitinol.

Figure 5F:
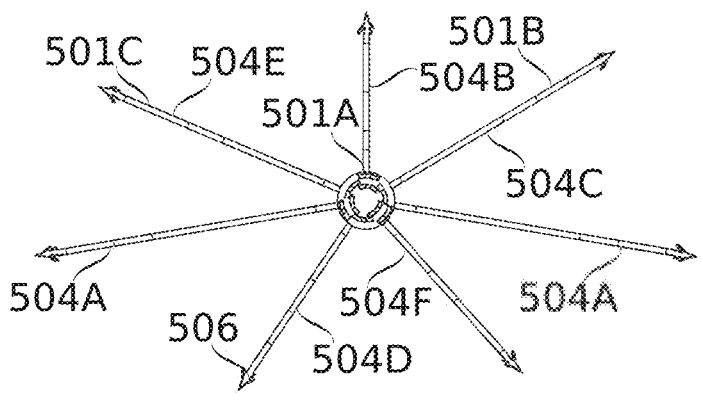

Reference is now made to FIGS. 5E-5F, which schematically illustrate assembled suturing clip 500 in an expanded configuration, according to some embodiments of the present disclosure.

The assembled suturing clip 500 shown in FIGS. 5E-5F appears in its extended state (which also happens to correspond, for example, to the state shown in FIG. 1A). From FIG. 5F in particular, it can be seen that anchors 506 are arrayed around an oval and/or elliptical perimeter. Optionally, the perimeter can be selected to be any suitable shape for anchoring.

During deployment, this state is maintained by holding the bases of the arms straight by a constraining device (such as a surrounding lumen of deployment system 110). The unconstrained anchoring ends of the arms are predisposed (e.g., superelastically set) to assume the positions shown, starting from a constrained position, wherein all of the arms 504A-504F are collapsed (e.g., by containment within a lumen) to extend along the same longitudinal direction as is shown for their bases. Thus, deployment begins with suturing clip in a first, collapsed delivery position, and proceeds to a second, expanded anchoring position.

In the extended state, suturing clip 500 is in a configuration suitable for establishing anchoring with tissue, for example corresponding to FIG. 2G.

Figure 5G:
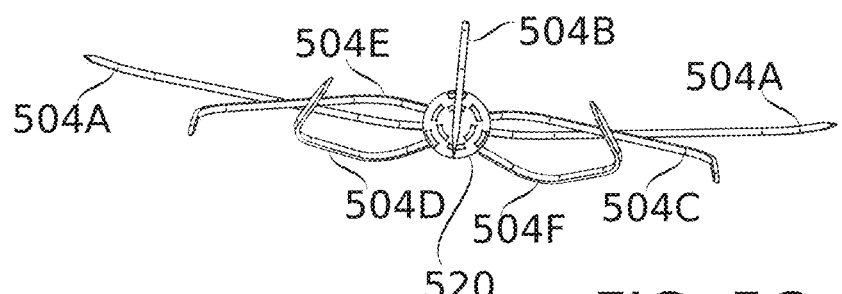
FIGS. 5G-5H schematically illustrate an assembled suturing clip in an everted configuration, according to some embodiments of the present disclosure.
Figure 5H:
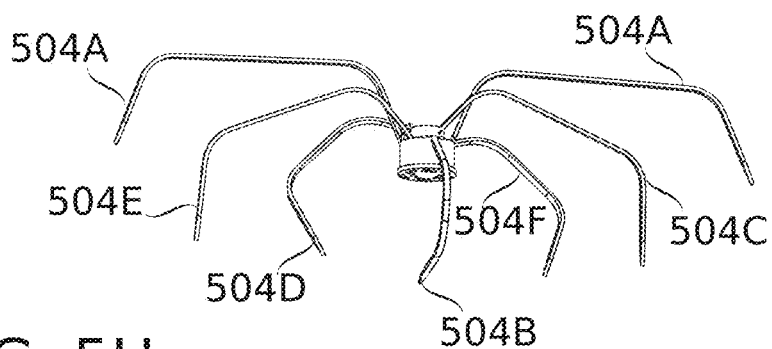

Reference is now made to FIGS. 5G-5H, which schematically illustrate assembled suturing clip 500 in an everted configuration, according to some embodiments of the present disclosure. Upon removal of constraints on movement of the bases of arms 504A-504F, the arms continue their rotations (largely impelled, in some embodiments, by torsion of torsion bars 530, 532, 534), moving from the expanded anchoring position of FIGS. 5E-5F into the collapsed suturing configuration of FIGS. 5G-5H. In this configuration, the arms are everted, to the extent that their anchors 506 end up positioned on the side of the core parts (e.g., connecting disk 520) opposite that on which they started. Illustration of barbs 506 has been suppressed in FIGS. 5G-5H.

It may also be noted that there is again a "zigzag" suturing band established by arms 104A-104F, as has also been described in relation to other embodiments herein. In the illustrated orientation of suturing clip 500, the anchoring end of arm 504B crosses from top to bottom, as do the anchoring ends of arms 504B and 504E. They interdigitate with arms 504D, 504F (which cross from bottom to top), and with arms 504A on either side, which also cross upward.

Reference is now made to FIGS. 6A-6D, which schematically illustrate torsion bar arm mountings, according to some embodiments of the present disclosure. In some embodiments, any of arms 504A-504F (and optionally any arm of any other embodiment described herein) connects to the suturing clip core through a torsion bar, e.g., torsion bar 530. Each of FIGS. 6A-6D shows just a single arm subassembly 501A, with two of the arms 504A fixed in their expanded anchoring configurations in order to emphasize movements of arm 504B due to twisting of torsion bar 530. In FIG. 6A and the detail view of FIG. 6C, torsion bar 530 is shown in its constrained position. Once constraint is removed, torsion bar 530 is free to twist arm 504B so that it ends up underneath core region 502A, as shown in FIG. 6B and in detail in FIG. 6D. The twisting potentially achieves a large relative positional shift of the anchoring end of arm 504B, even if arm 504B itself does not undergo any further conformational changes of its own when left unconstrained.

Torsion bar 530 (and the other torsion bars) provide a potential advantage for achieving reliable closure, insofar as torsion bars in a superelastic alloy are capable of exerting considerable force. It should also be noted that different torsion bars (e.g., comparing torsion bars 530, 531) can be oriented to move arms through rotational movements in different planes. This provides a potential advantage for supporting the three-configuration deployment series which proceeds from the first, collapsed delivery configuration, through to the second, expanded anchoring configuration, and finally to a third, collapsed suturing configuration. Each configuration is optionally shaped to place the anchoring ends of the arms in different positions, not only with respect to the core, but also with respect to each other. For example, the anchoring ends of the arms move from a perimeter-like configuration in the expanded anchoring configuration to an interdigitated configuration in the collapsed suturing configuration.

Reference is now made to FIGS. 7A-7F, which schematically illustrate suturing clip 500 in three different stages of deployment, each from two different viewing angles, according to some embodiments of the present disclosure.

Figure 7A:
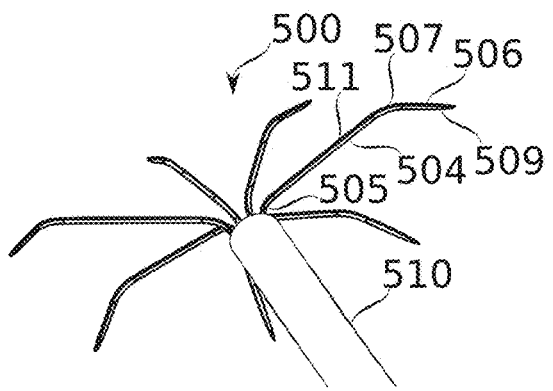
FIGS. 7A-7F schematically illustrate a suturing clip in three different stages of deployment, each from two different viewing angles, according to some embodiments of the present disclosure.
Figure 7B:
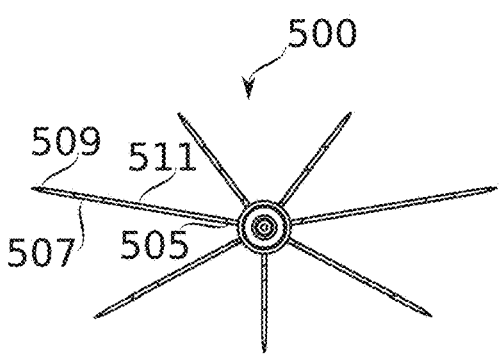

FIGS. 7A-7B show suturing clip 500 in the expanded anchoring configuration, from a perspective view (FIG. 7A) and a distal-to-proximal view (FIG. 7B). In this configuration, each arm optionally comprises a pair of bends; basal bend 505 near the core 502, and anchor bend 507 nearer to anchoring end of the arms. Optionally, this creates for each arm an anchoring segment 509 (carrying an anchor 506), a middle segment 511 between the two bends 505, 507, and optionally a base segment 517 which is basal on arm 504 relative to basal bend 505. Optionally, each of bends 505, 507 bends within a shared plane for a given arm 504. Moreover, for example as can be seen from the view of FIG. 7B, the bends 505, 507 are optionally within a multiplicity of planes sharing a common axis (as shown, the axis of the radial center of a distal portion of the delivery system 110). This tends to orient the anchors 106 so that they face radially outward for contacting tissue of ostium 3.

While these properties of bending direction potentially yield a convenient configuration for simplicity of manufacture and/or effectiveness of anchoring, embodiments of the present disclosure are not limited to have these properties. For example, bends 505, 507 of an arm 504 optionally bend in different planes, e.g., due to a twist in the superelastically set shape at some point along intermediate segment 511. Also optionally, bends 505, 507 of different arms 504 bend in a multiplicity of planes lacking a common axis.

Figure 7C:
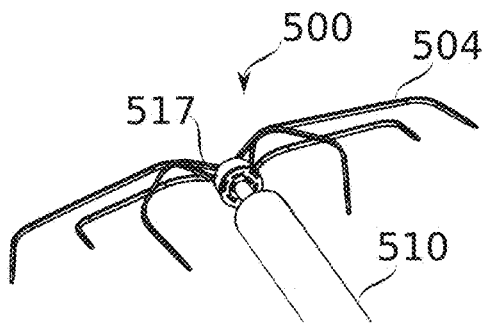
Figure 7D:
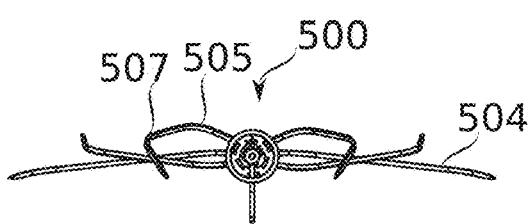
Figure 7E:
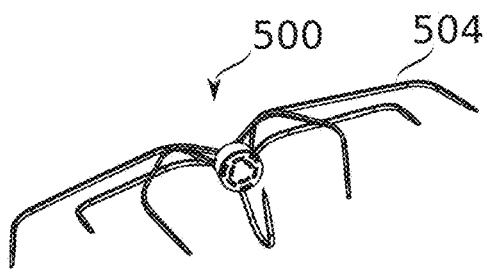
Figure 7F:
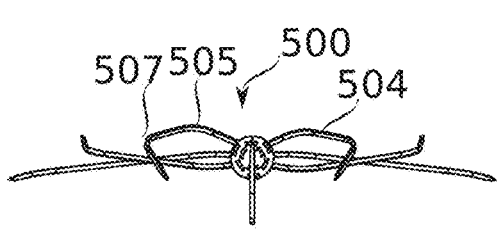

FIGS. 7C-7D show suturing clip 500 in the collapsed suturing configuration, from a perspective view (FIG. 7C) and a distal-to-proximal view (FIG. 7D), with the delivery system 110 still attached. FIGS. 7E-7F show suturing clip 500 in the same collapsed suturing configuration, from a perspective view (FIG. 7E) and a distal-to-proximal view (FIG. 7F), with the delivery system 110 detached.

It may be noted that now the bends 505, 507 can be seen for some of the arms 504 as having shifted in their planar orientation. In the embodiment shown, this is achieved by twisting of torsion bars 530, which are themselves longitudinally oriented in different directions. For example, some torsion bars 530 optionally extend longitudinally parallel to a plane of connecting disk 520. Others (e.g., as illustrated for torsion bars 532, 534) extend obliquely to connecting disk 520; e.g., obliquely at an angle of about 20°, 30°, 45°, or another angle.

The number of degrees of freedom available for the multiply-jointed arms has a potential advantage in allowing the positions of anchors 506 in the expanded anchoring configuration to be decoupled from positions of the same anchors 506 in the collapsed suturing configuration. For each configuration and its functions, an optimal pattern of anchor positions can be determined, motion through the degrees of freedom available is adjusted correspondingly in the design and manufacture of the joints to create a suturing clip which transitions automatically between the determined patterns of anchor positions.

The collapsing motion to reach the suturing configuration is optionally isolated in time from motion to reach the expanded anchoring configuration of FIGS. 7A-7B by initially retaining constraint (e.g., by distal catheter end 112) on just the core 502, after retraction of the constraint proximally past bends 507 and then bends 505. Then, further proximal retraction removes the constraint on motion, allowing the torsion bars 530 to actuate. Motion through bends 507 and 505 can be similarly separated in time, optionally producing three distinct stages of deployment: a first bending to spread the anchoring segments 509, a second bending to produce the deployed anchoring configuration of FIGS. 7A-7B, and a third bending to produce the collapsed suturing configuration of FIGS. 7C-7F. Correspondingly, there may be said to exist three "joints" per arm 504—bends 505, 507 along the arm 504, and torsion bar 530.

It should be noted, moreover, that the motions can also be sequentially reversed by advancing constraint (e.g., by distal catheter end 112) again back over the arms 104.

It may readily be understood that another number of joints per arm of a suturing clip 100 may be provided, in some embodiments. The joints are optionally shaped (e.g., superelastically set) to provide any suitable combination of planar and torsion movements to assume a plurality (optionally a multiplicity) of well-defined configurations at initial, final, and/or intermediate stages of deployment.

Figure 7G:
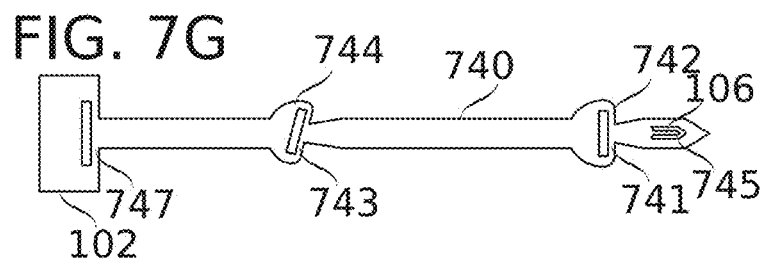
FIG. 7G schematically illustrates a portion of a suturing clip (only one arm is shown) comprising an arm attached to a core, in which bending of arm is around one or more torsion bars, including torsion bars which are positioned along the longitudinal extent of the arm, according to some embodiments of the present disclosure.

Reference is now made to FIG. 7G, which schematically illustrates a portion of a suturing clip 100 (only one arm is shown) comprising an arm 740 attached to a core 102, in which bending of arm 740 is around one or more torsion bars 741, 743, 747, including torsion bars 741, 743 which are positioned along the longitudinal extent of the arm 740. The torsion bars 741, 743 are optionally created by cutting the bar shape from "elbows" 742, 744 of the arm 740. As for torsion bars 530, 532, 534, the torsion bar angle can be adjusted to change the plane of bending and/or final orientation of segments of arm 740. Also shown is anchor cutout 745, which illustrates a method of manufacturing an anchor 106—the arm blank is cut (e.g., laser-cut) with a slit extending on either side of a central spike (which optionally forms the anchor 106). The spike is superelastically set to protrude from the arm tip when unconstrained, and flattened to lie within the arm 740 otherwise. It should be understood that arms 740 using the torsion bar elbow 742 are optionally used in place of any arm 104 of another suturing clip described herein, for example, in place of any arm 504.

Suturing Clips with Self-Collapsing, Branched Arms

Reference is now made to FIGS. 8A-8G, which schematically illustrate everting-type closure suturing clip 800 comprising arm subassemblies 807, 808, according to some embodiments of the present disclosure. Suturing clip 800 is an embodiment of a suturing clip 100.

Suturing clip 800 comprises arm subassemblies 807, 808, each comprising a plurality of arms 804 joined through an arm assembly trunk 811 to core 802.

Bends in arms 805, 809 are exposed by withdrawal of constraint from catheter distal end 112 of delivery system 810, allowing expansion of suturing clip 800 to an expanded anchoring configuration. The expanded anchoring configuration is in FIGS. 8A-8C from distal-to-proximal looking, side, and side-oblique perspectives, respectively. Expansion creates an arrangement of anchors 806 wherein each arm assembly 807, 808 spreads its anchoring ends to define a partial perimeter, for example as described in relation to suturing clip 400. In the expanded configuration, anchors 806 are held in a position which allows them to be inserted into tissue of the ostium 3 of LAA 1 by manipulation of delivery system 110.

Closure of suturing clip 800 (e.g., after anchoring) is everting-type, as illustrated in FIGS. 8D-8G. Eversion of suturing clip 800 is accomplished by further withdrawal of constraint, e.g., by catheter distal end 112, exposing trunk 811. Upon removal of constraint, trunk 811 bends (e.g., is superelastically set to bend) through an everting turn (which may be 180° or more).

Figure 8A:
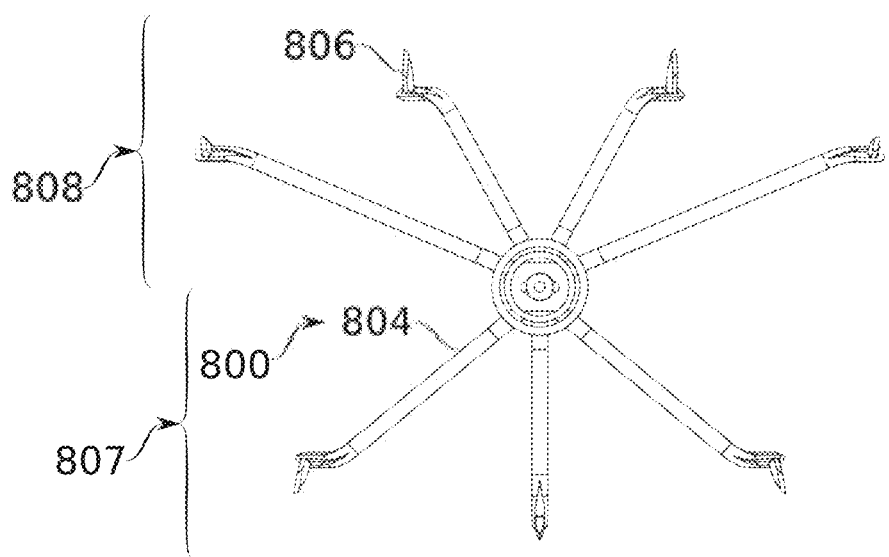
FIGS. 8A-8G schematically illustrate an everting-type closure suturing clip comprising arm subassemblies, according to some embodiments of the present disclosure.
Figure 8B:
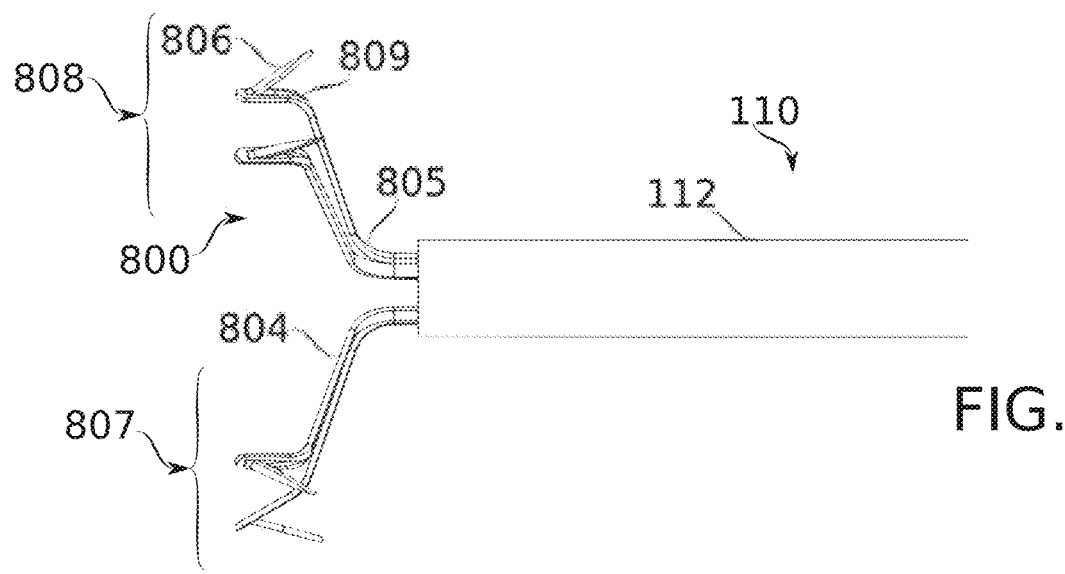
Figure 8C:
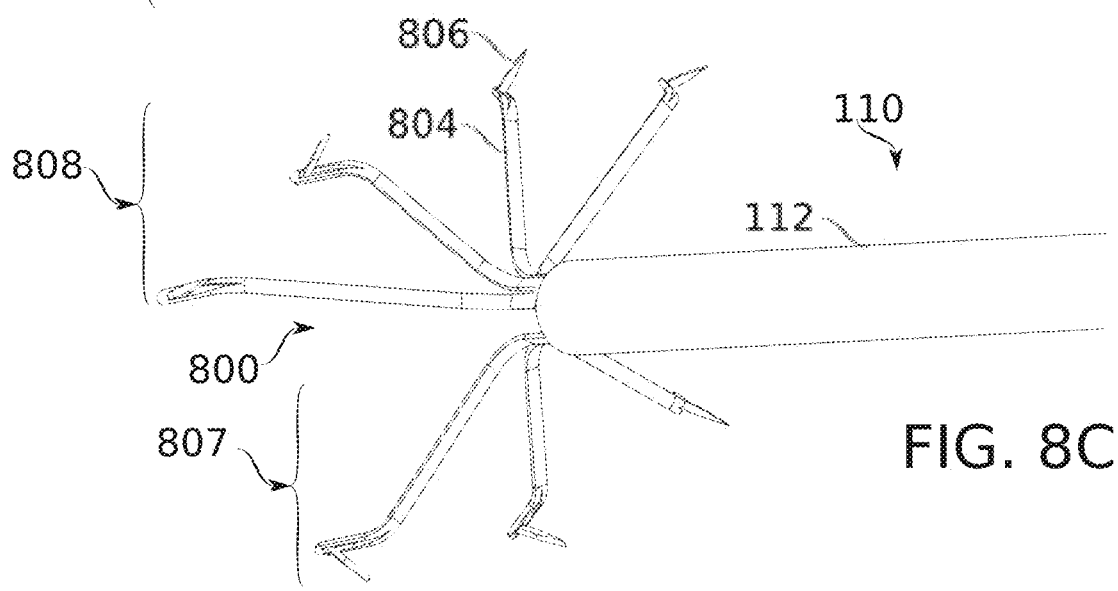
Figure 8D:
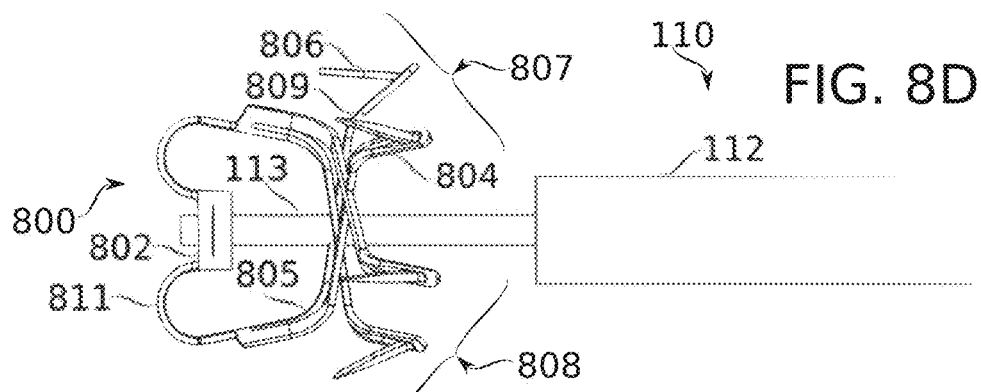
Figure 8E:
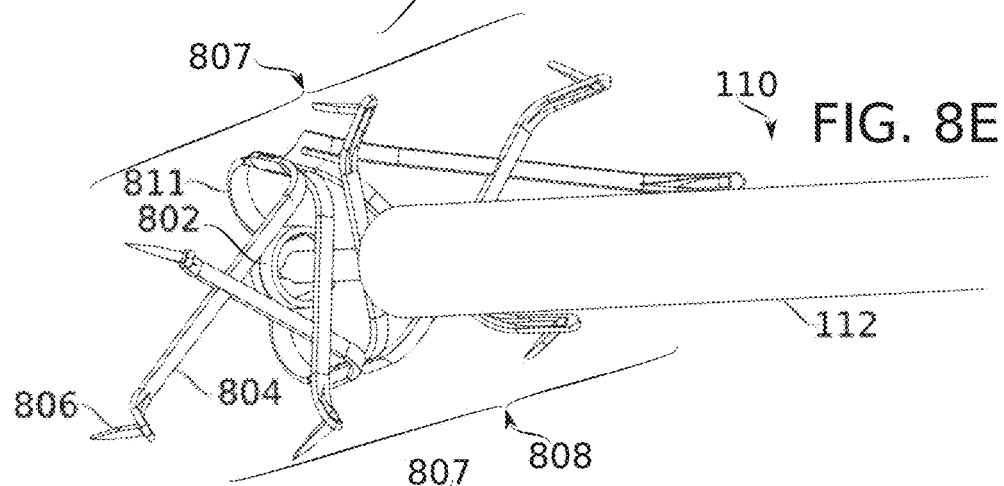
Figure 8F:
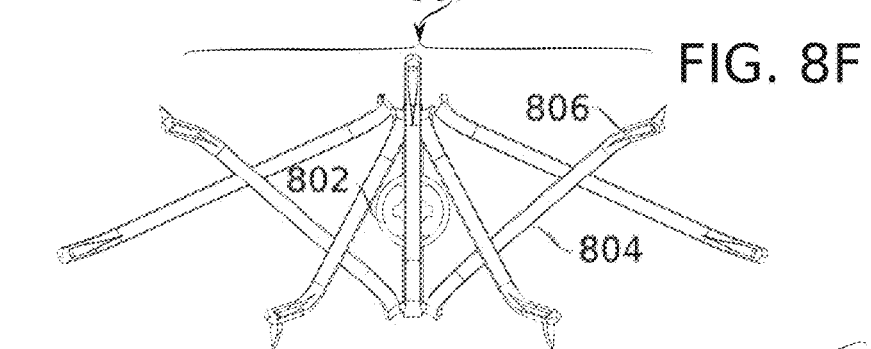
Figure 8G:
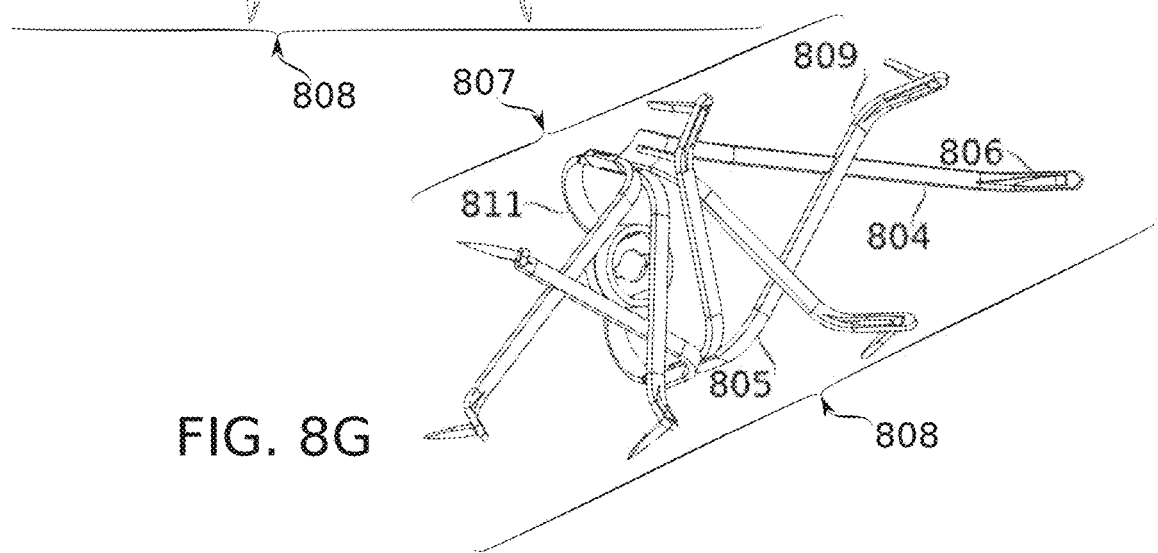

FIGS. 8D-8G show suturing clip 800 in its collapsed suturing configuration, from side, side-oblique, distal-to-proximal looking, and again side-oblique perspectives, respectively. In FIGS. 8D-8E, suturing clip 800 is attached to delivery system 110 via delivery mount 113, while in FIGS. 8F-8G, it is detached.

As also described for suturing clip 400, arms 804 of the arm subassemblies 807, 808 are positioned to interdigitate upon collapse to the collapsed suturing configuration. When attached to tissue, complete collapse to the illustrated configuration is potentially resisted by the bulks of two perimeter portions of the ostium 3 encountering each other. As a result, arms 804 continue to exert closing force, potentially helping to ensure a more complete and/or stable closure. The resulting line of closure may be a zigzag band, alternating between positions of the interdigitated arms 804 of the two arm subassemblies 807, 808.

Reference is now made to FIGS. 11A-11G, which schematically illustrate everting-type closure suturing clip 1100 comprising arm subassemblies 1107, 1108, according to some embodiments of the present disclosure. Suturing clip 1100 is an embodiment of a suturing clip 100.

Suturing clip 1100 comprises arm subassemblies 1107, 1108, each comprising a plurality of arms 1104 joined through an arm assembly trunk 1105 to core 1102. Conversion from a collapsed delivery configuration (FIG. 11A) through to a collapsed suturing configuration (FIGS. 11F-11G) optionally comprises one or both of bending motions of the arms 1104 (e.g., at bends 1109, and/or along trunk 1105), and torquing motions of torsion bars 1110.

Figure 11A:
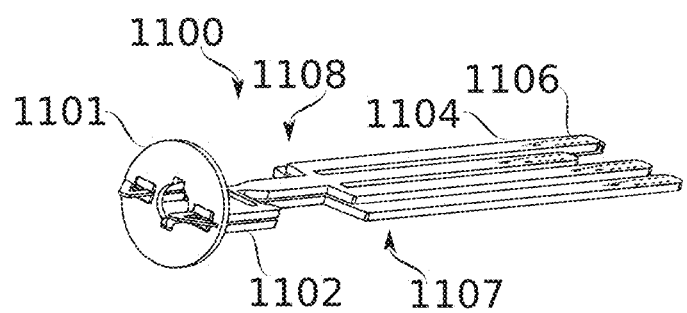
FIGS. 11A-11G schematically illustrate an everting-type closure suturing clip comprising arm subassemblies, according to some embodiments of the present disclosure.

In FIG. 11A, a collapsed delivery configuration is shown. Arm subassemblies 1107, 1108 are joined at core 1102 by connecting disk 1101. Optionally, each subassembly 1107, 1108 comprises a separate piece, which may be manufactured by cutting (e.g., laser cutting) from sheet of a superelastic material such as nitinol.

Bends of assembly trunk 1105 and along arms 1104 (for example, bend 1109) are exposed by withdrawal of constraint from catheter distal end 112 of delivery system 110 (not shown in these figures), allowing expansion of suturing clip 1100 to an expanded anchoring configuration.

Figure 11B:
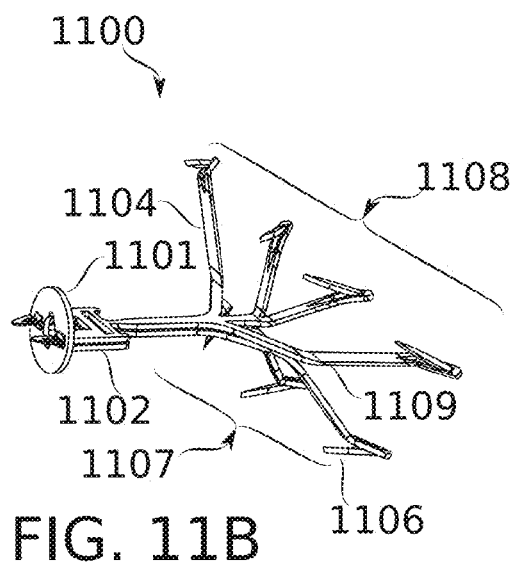
Figure 11C:
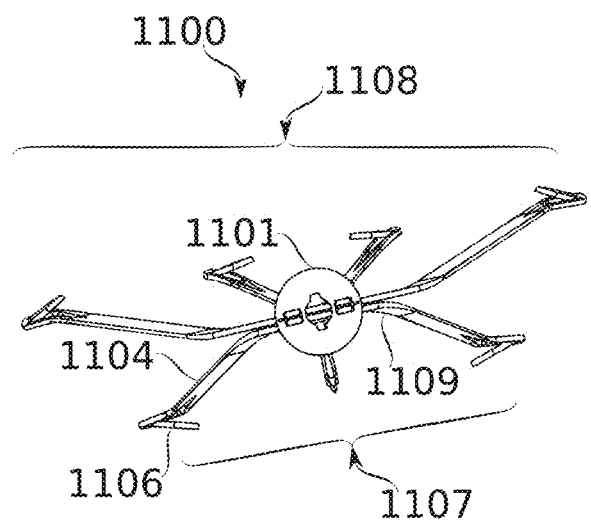

In some embodiments, an expanded anchoring configuration (FIGS. 11D-11E) is preceded by a partially-expanded positioning configuration. This configuration is shown in FIGS. 11B-11C, from side-oblique and distal-to-proximal looking perspectives, respectively.

In the partially-expanded positioning configuration constraint is partially removed, e.g., retracted to about the position where each trunk 1105 joins the individual segments of arm subassemblies 1107, 1108. Arms 1104 expand along a lateral axis to most of their full horizontal extent (e.g., at least 70%, 80%, 90%, or their full horizontal extent.

Arms 1104 expand along a vertical axis to a smaller fraction of their eventual full vertical extent, e.g., half or less, for example, about 30%, 40%, or 50% of their fully expanded vertical extent.

This provides a potential advantage by expanding enough to force the suturing clip 1100 to be centered in the LAA, while still remaining sufficiently un-expanded enough that anchoring is not induced. An overtube 111 can be pushed forward again to re-constrain the suturing clip 1100, and it can be re-collapsed potentially with a low risk of tearing due to being already embedded in tissue (e.g., of the ostium 3 of LAA 1). This assists repeated expanding a collapsing which may be performed in the course of ensuring that the device is properly positioned before full expansion and device anchoring is established.

Figure 11D:
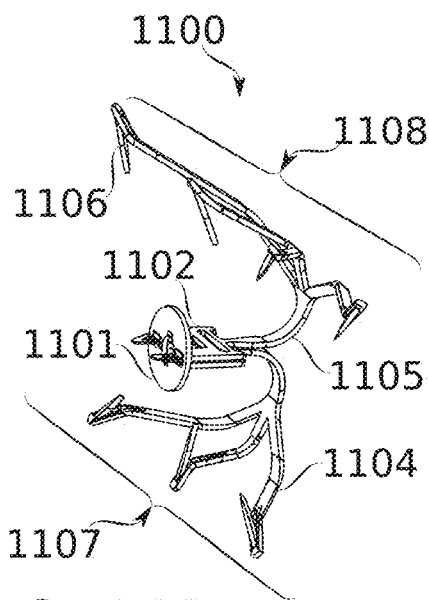
Figure 11E:
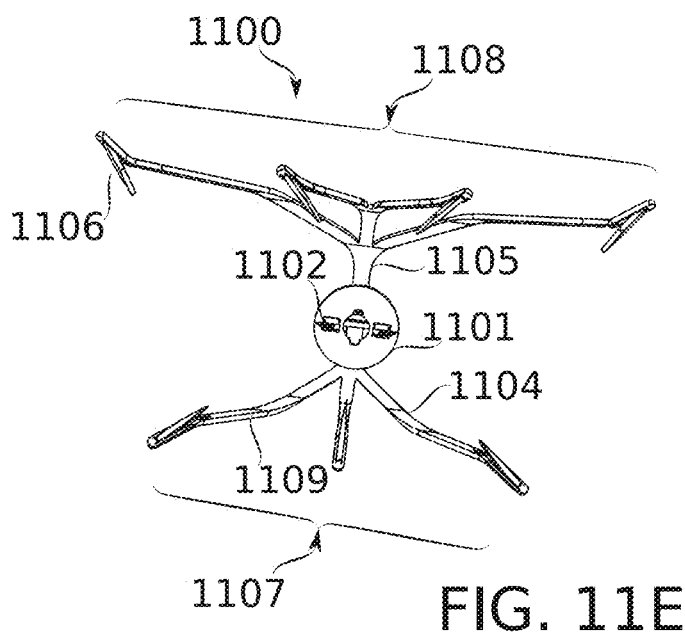

A later stage representing an expanded anchoring configuration is shown in FIGS. 11D-11E from side-oblique and distal-to-proximal looking perspectives, respectively. At a stage of expansion between that of FIGS. 11B-11C and FIGS. 11D-11E, there may be contact of anchors 1106 with tissue; and then as expansion continues, anchors 1106 "roll over", not only dragging tissue with them, but also potentially gaining further purchase and/or insertion as they change their angle of pulling to one that the tissue resists.

Expansion creates an arrangement of anchors 1106 wherein each arm assembly 1107, 1108 spreads its anchoring ends to define a partial perimeter, for example as described in relation to suturing clip 400. In the expanded configuration, anchors 1106 are held in a position which allows them to be inserted into tissue of the ostium 3 of LAA 1 by manipulation of delivery system 110.

Figure 11F:
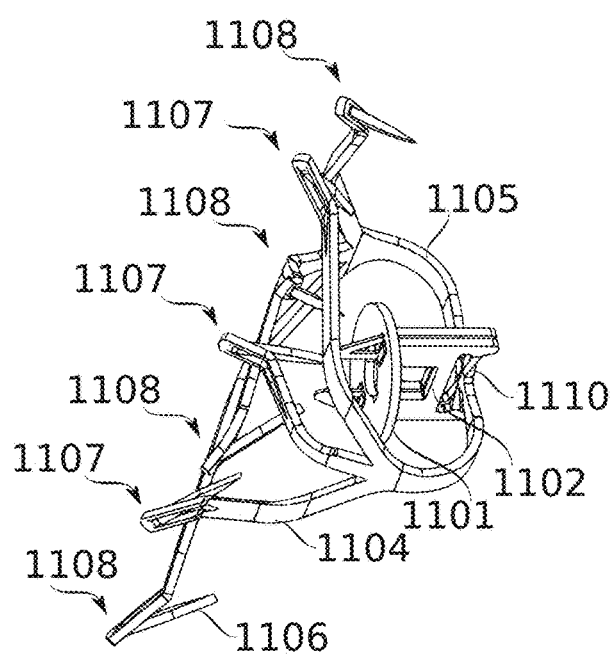
Figure 11G:
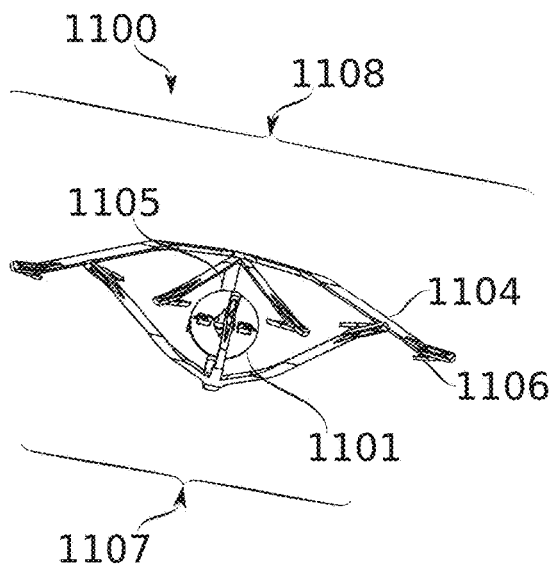

FIGS. 11F-11G show suturing clip 1100 in its collapsed suturing configuration, from side-oblique and distal-to-proximal looking perspectives, respectively. Closure of suturing clip 1100 (e.g., after anchoring) is everting-type. Eversion of suturing clip 1100 is accomplished by further withdrawal of constraint, e.g., by catheter distal end 112, exposing trunk 1105. Upon removal of constraint, trunk 1105 bends (e.g., is superelastically set to bend) through an everting turn (which may be 180° or more).

This motion, in some embodiments, comprise motions induced by torquing of torsion bars 1110. Comparison of FIGS. 11A and 11F, for example, illustrates torsion bars 1110 which have torqued about 90° over the course of deployment. The use of torsion bars 1110 can result in the storage of considerable force by concentrating strain movements into a relatively small area.

As also described for suturing clip 400, arms 1104 of the arm subassemblies 1107, 1108 are positioned to interdigitate upon collapse to the collapsed suturing configuration. Interdigitation can be with overshoot (to form a pronounced zigzag), or, as shown, toward a more linear configuration. When attached to tissue, complete collapse to the illustrated configuration is potentially resisted by the bulks of two perimeter portions of the ostium 3 encountering each other. As a result, arms 1104 continue to exert closing force, potentially helping to ensure a more complete and/or stable closure. Anchoring along the resulting line of closures alternates between positions of the interdigitated arms 1104 of the two arm subassemblies 1107, 1108.

Spreader for Use with a Suturing Clip

Reference is now made to FIGS. 9A-9F, which illustrate a sequence of operations wherein a tissue spreader 1000 is used together with a delivery system 910 to assist access to LAA 1 for insertion of a suturing clip 100, according to some embodiments of the present disclosure. Delivery system 910 is an example of a delivery system 110. Suturing clip 100 is illustrated as having reverting-type closure, similar to suturing clip 300. It should be understood, however, that features of delivery system 910, including tissue spreader 1000, are optionally provided together with any suturing clip design, for example any of the reverting-type closure suturing clips 300, 350, 400, and/or the everting-type closure suturing clips 500, 800, 1100 described herein.

Figure 9A:
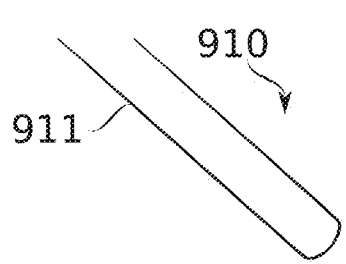
FIGS. 9A-9F illustrate a sequence of operations wherein a tissue spreader is used together with a delivery system to assist access to LAA for insertion of a suturing clip, according to some embodiments of the present disclosure.
Figure 9B:
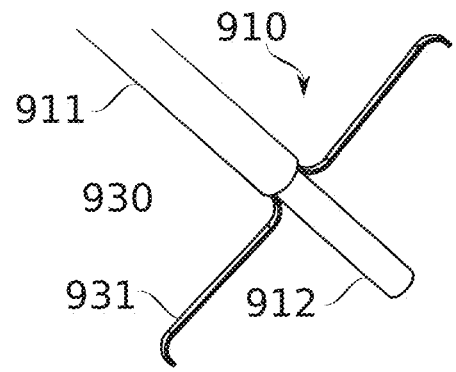
Figure 9C:
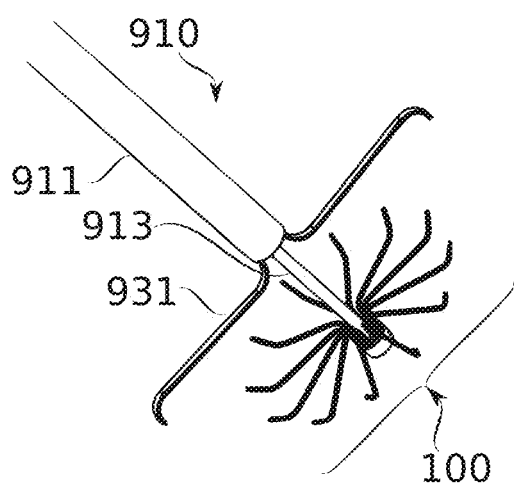

FIG. 9A illustrates catheter overtube 911. In FIG. 9B, catheter distal end 912 has been advanced distally forward from catheter overtube 911, with suturing clip 100 inside it. Also advanced distally forward are the arms of spreader 1000, the parts and operation of which is discussed further in relation to FIGS. 10A-10C. In FIG. 9C, suturing clip 100 is exposed beyond spreader 1000 on delivery mount 913, after withdrawal of distal catheter end 912.

In overview, spreader 1000 engages tissue in or near an ostium 3 of an LAA 1 to perform one or more of: (1) opening the aperture (in the direction of spreading) to allow insertion of a suturing clip 100, 2) shaping the aperture to a shape which is suitable for engagement with the expanded anchoring configuration of the suturing clip 100, (3) centering and/or orienting the device in the ostium 3 of the LAA 1, and (4) closing the ostium 3 in another direction (which potentially collapses along an axis orthogonal to the direction of spreading), potentially increasing contact force with anchors 106 of suturing clip 100. The collapse is due to the perimeter of ostium 3 being strained in the direction of spreading.

Figure 9D:
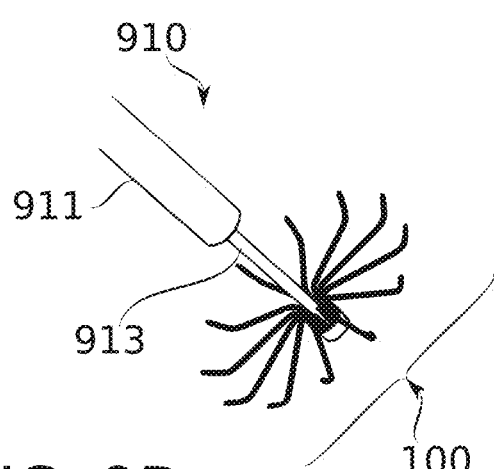
Figure 9E:
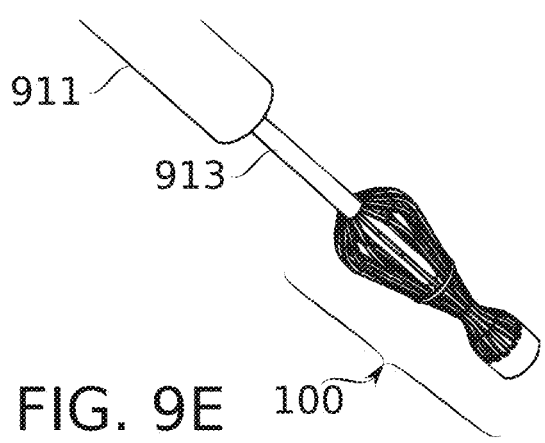
Figure 9F:
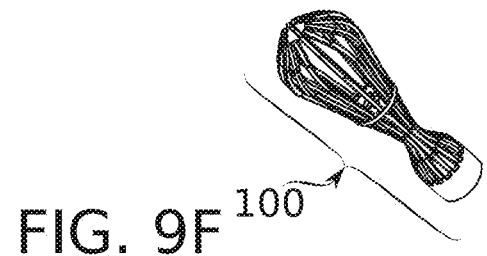

Once suturing clip 100 is in place (optionally also after anchoring), spreader 1000 is withdrawn again, for example as shown in FIG. 9D. Closure of suturing clip 100 continues through stages already described, for example proximal movement of closure disk 120 (FIG. 9E), and detachment of delivery mount 913 (FIG. 9F). This closure sequence is optionally substituted in some embodiments, e.g., by the progressive eversion of a suturing clip 100 having everting-type closure.

Figures 10A, 10B:
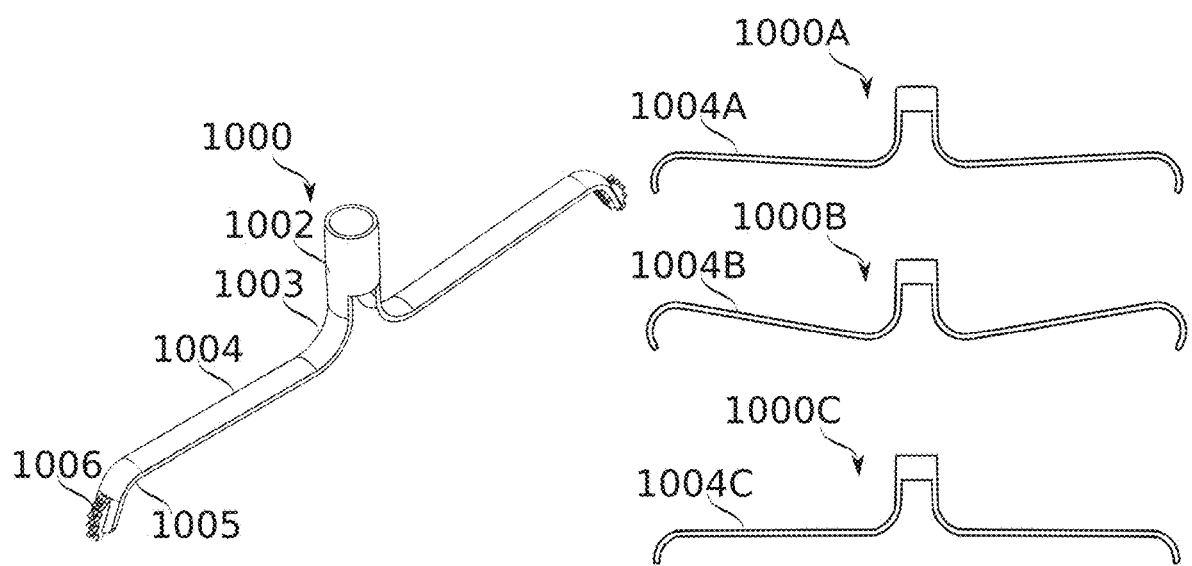
FIGS. 10A-10C schematically illustrate aspects of design of various tissue spreaders, according to some embodiments of the present disclosure.
Figure 10C:
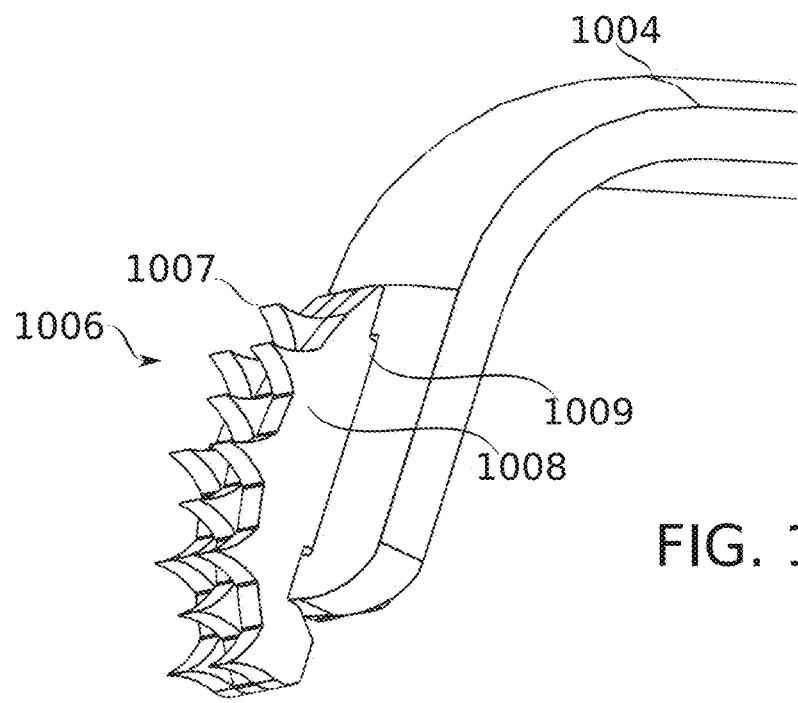

Reference is now made to FIGS. 10A-10C, which schematically illustrate aspects of design of various tissue spreaders 1000, 1000A, 1000B, 1000C, according to some embodiments of the present disclosure.

FIG. 10A shows elements of a tissue spreader 1000, including spreader arms 1004 attached to spreader core 1002. Each arm 1004 comprises a grip 1006 at its free end. Each arms 1004 further comprises a basal bend 1003 near where arm 1004 attaches to core 1002, and a distal bend 1005 which re-orients a tip of arm 1004 so that grip 1006 is oriented radially outward to contact lumenal tissue when spreader 1000 is expanded.

Spreader 1000 is formed, in some embodiments, from a superelastic alloy such as nitinol, allowing it to be packaged for delivery within, e.g., catheter overtube 911. It is superelastically set to assume the configuration, e.g., of FIG. 10A when constraint on its expansion is removed.

FIG. 10B illustrates other arm designs 1004A, 1004B, 1004C for a tissue spreader 1000A, 1000B, 1000C. The arm designs differ in aspects of the amount of curvature at their ends (where grip 1006 may be placed), and/or in the angle to which their expanded forms bend relative to a longitudinal axis of a distal portion of delivery system 110.

With greater end curvature, there is potentially more assurance that a rounded tip surface will encounter tissue, rather than the end, with a concomitant reduction in a potential for accidental perforation. Designs with greater re-curvature beyond perpendicular to the longitudinal axis of the distal portion of delivery system 110 potentially exhibit less stiffness for stretching, but potentially also a reduced chance for perforation.

FIG. 10C illustrates a design for a grip 1006, comprising one or more roughened (e.g., ridged and/or toothed) plates 1008. The plates 1008 are optionally set into an aperture 1009 of arm 1004, and secured by crimping and/or welding. Optionally, ridges and/or teeth 1007 are offset from each other on adjacent different plates. In some embodiments, roughening of the grip surface is by another method, for example, machining of a thickened end of arm 1004. Preferably, grip 1006 is rough enough to engage with a surface of the tissue, but not so sharp, penetrating and/or abrasive as to cause it damage.

General

Reference is now made to FIG. 1A, which schematically illustrates a suturing clip 100 engaged to tissue within a LAA 1, according to some embodiments of the present disclosure.

Reference is also made to FIG. 1B, which schematically illustrates the suturing clip 100 of FIG. 1A in an expanded configuration suitable for tissue engagement, according to some embodiments of the present disclosure.

reference is made to FIG. 1C, which schematically illustrates a suturing clip 100 which has engaged tissue within an LAA 1 and then undergone a conformational change to close an LAA ostium 3, according to some embodiments of the present disclosure.

Reference is also made to FIG. 1D, which schematically illustrates the suturing clip 100 of in the LAA-closing conformation of FIG. 1C, according to some embodiments of the present disclosure.

Reference is now made to FIG. 1E, which schematically illustrates a trans-septal approach insertion of a suturing clip 100 using a delivery system 110, according to some embodiments of the present disclosure.

Reference is now made to FIG. 1F, which is a schematic flowchart of a method of inserting of a suturing clip 100 using a delivery system 110, according to some embodiments of the present disclosure.

Reference is now made to FIGS. 2A-2I, which schematically illustrate stages in the deployment of a suturing clip 100, according to some embodiments of the present disclosure.

Reference is now made to FIGS. 2J-2L, which schematically illustrate movements 203, 205, 203A, 203B, 205A, 205B of anchoring positions 201, 201A, 201B over the course of a transition of a suturing clip 100 between a deployed- and-anchored configuration, and a collapsed suturing configuration, according to some embodiments of the present disclosure.

Reference is now made to FIGS. 2M-2P, which illustrate details of interactions between a delivery system 110 and a suturing clip 100, according to some embodiments of the present disclosure.

Reference is now made to FIG. 3A, which schematically illustrates an expanded configuration of a reverting core-and-arm assembly 301 of a suturing clip 300, according to some embodiments of the present disclosure.

Reference is also made to FIG. 3B, which schematically illustrates suturing clip 300 an expanded configuration, including closure disk 320, according to some embodiments of the present disclosure.

Reference is now made to FIG. 3C, which schematically illustrates suturing clip 300 in a re-collapsed suturing configuration, collapsed by movement of closure disk 320, according to some embodiments of the present disclosure, and Reference is made to FIG. 3D, which schematically illustrates suturing closure disk 320, according to some embodiments of the present disclosure.

Reference is now made to FIG. 3E, which schematically illustrates an expanded configuration of a reverting core-and-arm assembly 351 of a suturing clip 350, according to some embodiments of the present disclosure.

Figure 3H:
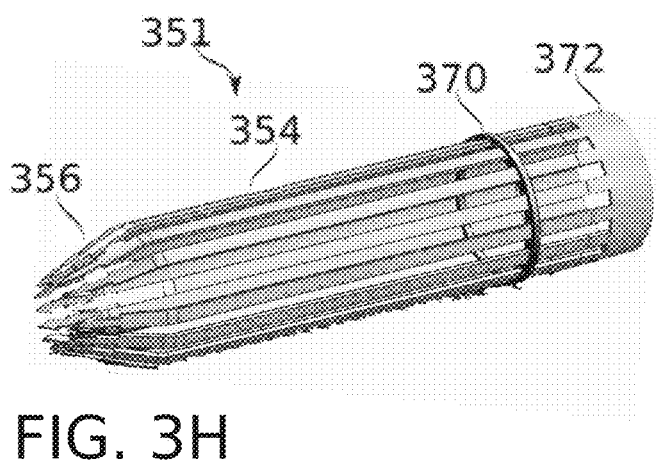
FIG. 3H schematically illustrates a suturing clip in a re-collapsed suturing configuration, collapsed by movement of closure disk, according to some embodiments of the present disclosure.

Reference is also made to FIGS. 3F-3G, which schematically illustrate suturing clip 350 an expanded configuration, including closure disk 370, according to some embodiments of the present disclosure.

reference is made to FIG. 3H, which schematically illustrates suturing clip 350 in a re-collapsed suturing configuration, collapsed by movement of closure disk 370, according to some embodiments of the present disclosure.

Figure 3I:
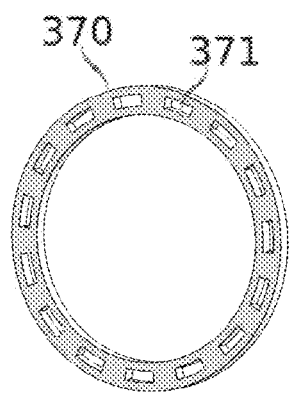
FIG. 3I schematically illustrates a suturing closure disk, according to some embodiments of the present disclosure.

Reference is now made to FIG. 3I, which schematically illustrates suturing closure disk 370, according to some embodiments of the present disclosure.

Reference is now made to FIG. 4A, which schematically illustrate an expanded configuration of a core-and-arm assembly 401 of a suturing clip 400, according to some embodiments of the present disclosure.

Reference is also made to FIG. 4B, which schematically illustrates suturing clip 400 an expanded configuration, including closure disk 420, according to some embodiments of the present disclosure.

Figure 4C:
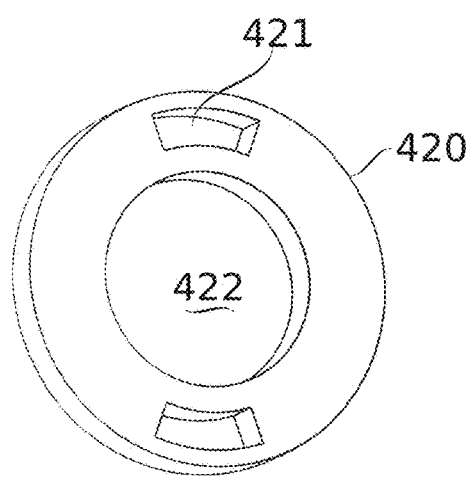
FIG. 4C schematically illustrates a suturing closure disk, according to some embodiments of the present disclosure.
Figure 4G:
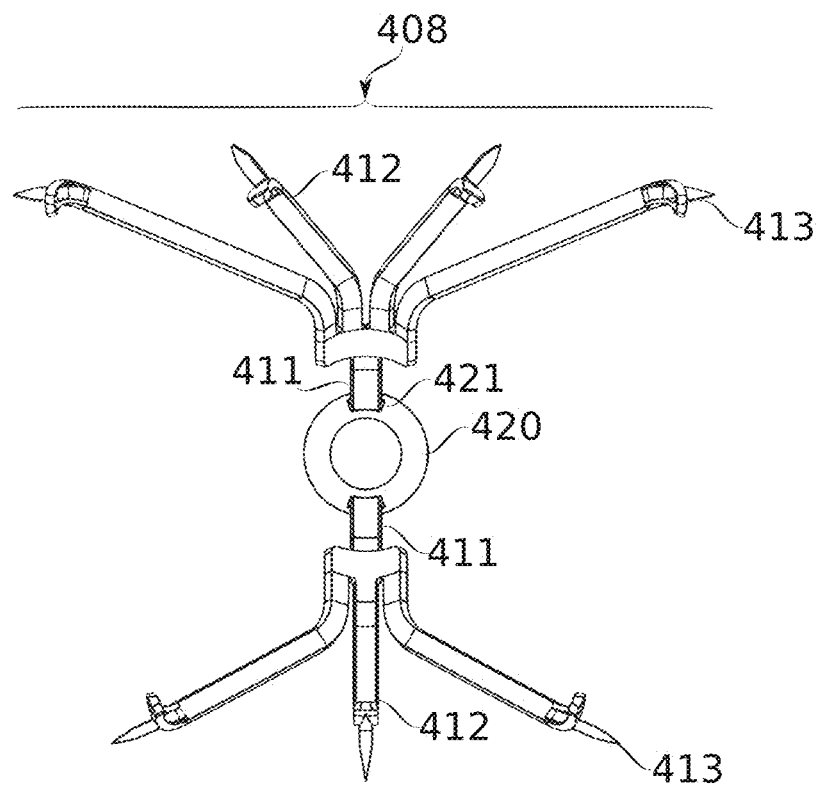
Figure 4H:
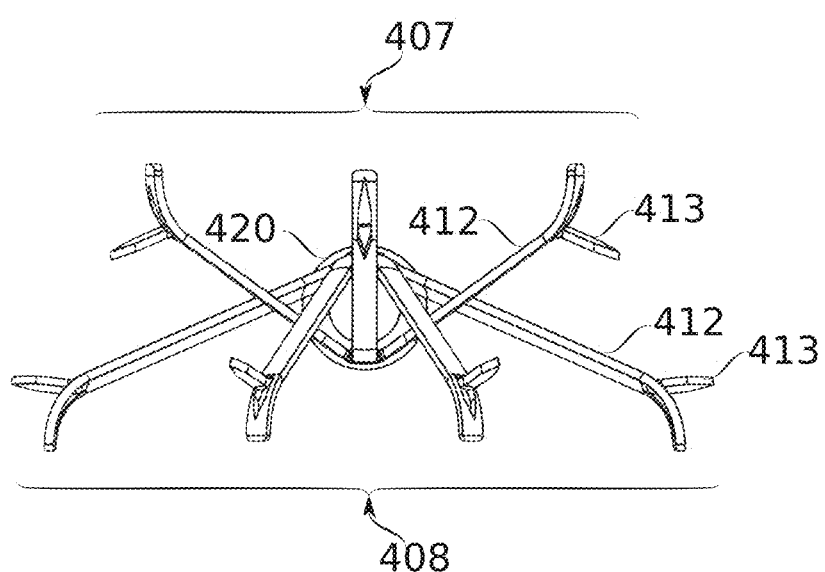

Reference is made to FIG. 4C, which schematically illustrates suturing closure disk 420, according to some embodiments of the present disclosure.

Reference is now made to FIGS. 4D-4H, which show deployment of suturing clip 400 under control of a deployment system 410, including deployment member 415, according to some embodiments of the present disclosure.

Reference is now made to FIGS. 5A-5D, which schematically illustrate parts of an everting suturing clip 500, according to some embodiments of the present disclosure.

Reference is now made to FIGS. 5E-5F, which schematically illustrate assembled suturing clip 500 in an expanded configuration, according to some embodiments of the present disclosure.

Reference is now made to FIGS. 5G-5H, which schematically illustrate assembled suturing clip 500 in an everted configuration, according to some embodiments of the present disclosure.

Reference is now made to FIGS. 6A-6D, which schematically illustrate torsion bar arm mountings, according to some embodiments of the present disclosure.

Reference is now made to FIGS. 7A-7F, which schematically illustrate suturing clip 500 in three different stages of deployment, each from two different viewing angles, according to some embodiments of the present disclosure.

Reference is now made to FIG. 7G, which schematically illustrates a portion of a suturing clip 100 (only one arm is shown) comprising an arm 740 attached to a core 102, in which bending of arm 740 is around one or more torsion bars 741, 743, 747, including torsion bars 741, 743 which are positioned along the longitudinal extent of the arm 740.

Reference is now made to FIGS. 8A-8G, which schematically illustrate everting-type closure suturing clip 800 comprising arm subassemblies 807, 808, according to some embodiments of the present disclosure.

Reference is now made to FIGS. 9A-9F, which illustrate a sequence of operations wherein a tissue spreader 1000 is used together with a delivery system 910 to assist access to LAA 1 for insertion of a suturing clip 100, according to some embodiments of the present disclosure.

Reference is now made to FIGS. 10A-10C, which schematically illustrate aspects of design of various tissue spreaders 1000, 1000A, 1000B, 1000C, according to some embodiments of the present disclosure.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the present disclosure may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments may be presented with reference to a range format. It should be understood that the description in range format is merely for convenience and brevity and should not be construed as an inflexible limitation on the scope of descriptions of the present disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although descriptions of the present disclosure are provided in conjunction with specific embodiments, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

It is appreciated that certain features which are, for clarity, described in the present disclosure in the context of separate embodiments, may also be provided in combination in a single embodiment. Conversely, various features, which are, for brevity, described in the context of a single embodiment, may also be provided separately or in any suitable subcombination or as suitable in any other described embodiment of the present disclosure. Certain features described in the context of various embodiments are not to be considered essential features of those embodiments, unless the embodiment is inoperative without those elements.

In addition, any priority document(s) of this application is/are hereby incorporated herein by reference in its/their entirety.

What is claimed is:

1. A suturing clip for closing a body lumen aperture defining a passageway into a portion of the body lumen, the passageway extending between a first side of the aperture to a second side of the aperture, and the suturing clip comprising:
    a core comprising a longitudinal axis extending from a proximal side of said core to a distal side of said core;
    a plurality of arms each joined at a basal side of the arm to a-said core of the suturing clip; and
    a respective anchor at a terminal end of each arm;
    wherein the suturing clip is configured to convert between:
    a collapsed delivery configuration expandable to attach the anchors to tissue within the portion of the body lumen and on the second side of the aperture,
    a collapsed suturing configuration shaped to re-position the anchors where they close the aperture and the passageway in directions leading both into and out of the portion of the body lumen,
    wherein the anchors close the passageway by movement of the attached tissue to a position that isolates the suturing clip from the first side of the body lumen aperture;
    wherein the suturing clip, in the collapsed delivery configuration, is configured to attach to a delivery mount and be advanced on the delivery mount from the first side of the body lumen aperture by distal movement along said longitudinal axis of the suturing clip; said distal movement being in a direction from said proximal side of said core to said distal side of said core;
    wherein said arms of the suturing clip, in said collapsed delivery configuration, extend in a proximal-distal configuration; where in said proximal-distal configuration said arms extend in a direction from said proximal side of said core to said distal side of said core in relation to said core and along said longitudinal axis;
    wherein said arms of the suturing clip are configured to transition from a proximal-distal configuration to a distal-proximal configuration; where in said distal-proximal configuration said arms extend in a direction from said distal side of said core to said proximal side of said core in relation to said core and during a transition between said collapsed delivery configuration to said collapsed suturing configuration; and
    wherein the suturing clip, in the collapsed suturing configuration, is positioned with the core and arms both isolated on the second side of the aperture.

2. The suturing clip of claim 1, wherein the suturing clip resiliently self-expands from the collapsed delivery configuration to an expanded anchoring configuration having a maximum diameter at least 5x larger than a maximum diameter of the suturing clip in the collapsed delivery configuration.

3. The suturing clip of claim 1, wherein the delivery mount is configured to be detached from the suturing clip in the collapsed suturing configuration and withdrawn through tissue closed by the anchors of the suturing clip to the first side of the closed tissue opposite the suturing clip isolated on the second side.

4. The suturing clip of claim 2, wherein the suturing clip is configured to resiliently self-collapse from the expanded anchoring configuration to the collapsed suturing configuration.

5. The suturing clip of claim 1, sized to be sheathed by a sheathing lumen of a trans-vascular catheter; and wherein the suturing clip in the collapsed delivery configuration is sheathed within the sheathing lumen.

6. The suturing clip of claim 5, wherein:
    the suturing clip is configured to resiliently self-expand from the collapsed delivery configuration to an expanded anchoring configuration upon a partial unsheathing from the sheathing lumen; and
    the suturing clip is configured to resiliently self-collapse from the expanded anchoring configuration to the collapsed suturing configuration upon a further unsheathing from the sheathing lumen.

7. The suturing clip of claim 6, wherein the suturing clip is configured to evert during converting between the collapsed delivery configuration and the expanded anchoring configuration, so that a side of the anchors which face radially inward in the collapsed delivery configuration faces outward in the expanded anchoring configuration.

8. The suturing clip of claim 6, having a proximal-to-distal axis, wherein the suturing clip is configured to evert during converting between the collapsed delivery configuration and the collapsed suturing configuration, so that a portion of the arms which is initially on a distal side of the core moves to a proximal side of the core.

9. The suturing clip of claim 6, wherein conversion from the expanded anchoring configuration to the collapsed suturing configuration comprises a reverting movement of the arms in a direction opposite a direction of their expansion from the collapsed delivery configuration to the expanded anchoring configuration.

10. The suturing clip of claim 5, further comprising a spreader, said spreader separately actuatable to extend laterally from the trans-vascular catheter, insert to the body lumen aperture, and configured to contact tissue of the body lumen aperture with grips to set a position of the sheathing lumen from which the suturing clip is deployed.

11. The suturing clip of claim 1, wherein the anchors, in the collapsed suturing configuration, define a zigzag pattern extending along a band of closure of the closed tissue.

12. The suturing clip of claim 1, wherein a first plurality of the arms extends from the core via a trunk which is shared in common by the plurality of the arms.

13. The suturing clip of claim 12, comprising a second plurality of arms, and wherein arms of the first plurality are configured to interdigitate with arms of the second plurality in the collapsed suturing configuration.

14. The suturing clip of claim 1, comprising a torsion bar, wherein at least one of the arms is mounted to at least one side of the torsion bar, and the torsion bar is configured to twist to move the at least one of the arms from the collapsed delivery configuration toward the collapsed suturing configuration.

15. The suturing clip of claim 1, wherein the anchors are positioned on a radially inward side of the arms in the collapsed delivery configuration, and move to a radially outward side of the arms during movement of the arms toward the collapsed suturing configuration.

16. A method of closing a body lumen aperture defining a passageway into a portion of the body lumen, the passageway extending between a first side of the aperture to a second side of the aperture, the method comprising:
    advancing a suturing clip attached to a delivery mount through the body lumen aperture from the first side of aperture to the second side of the aperture; said suturing clip comprising a longitudinal axis extending from a proximal side of said suturing clip to a distal side of said suturing clip;
    expanding the suturing clip at least partially on the second side of the body lumen aperture;
    anchoring tissue defining a perimeter of the body lumen aperture to anchors of the suturing clip; and
    collapsing the suturing clip so that the anchors close the body lumen aperture and the passageway in directions leading both into and out of the portion of the body lumen while the suturing clip remains on the second side of the closed aperture and isolated from the first side of the closed aperture;
    wherein a transition from said expanding to said collapsing comprises transitioning arms of said suturing clip from a proximal-distal configuration to a distal-proximal configuration; where in said proximal-distal configuration said arms extend in a direction from said proximal side of said suturing clip to said distal side of said suturing clip in relation to said suturing clip and along said longitudinal axis; and where in said distal-proximal configuration said arms extend in a direction from said distal side of said suturing clip to said proximal side of said suturing clip in relation to said suturing clip.

17. The method of claim 16, wherein the body lumen aperture is an ostium of a left atrial appendage.

18. The method of claim 16, wherein the collapsing comprises moving the anchors into a zigzag configuration.

19. The method of claim 16, wherein the collapsing comprises moving the anchors toward a common radial center.

20. The method of claim 16, wherein the collapsing comprises moving at least one of the anchors radially outward, while at least one of the anchors moves radially inward.

21. The suturing clip of claim 1, wherein the arms are sized to attach the anchors to aperture tissue of a left atrial appendage, and configured to collapse to a shape that closes the aperture the left atrial appendage.

\* \* \* \* \*